(12) United States Patent
Brown et al.

(10) Patent No.: US 10,131,488 B2
(45) Date of Patent: Nov. 20, 2018

(54) AEROSOL HAIRSPRAY PRODUCT COMPRISING A SPRAYING DEVICE

(71) Applicant: The Procter & Gamble Company, Cincinnati, OH (US)

(72) Inventors: Jodi Lee Brown, Cincinnati, OH (US); William Mercer Benson, Harrison, OH (US); Jose Antonio Carballada, Cincinnati, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 15/170,031

(22) Filed: Jun. 1, 2016

(65) Prior Publication Data

US 2016/0347536 A1 Dec. 1, 2016

Related U.S. Application Data

(60) Provisional application No. 62/169,085, filed on Jun. 1, 2015.

(51) Int. Cl.
*B65D 83/14* (2006.01)
*A61Q 5/06* (2006.01)
(Continued)

(52) U.S. Cl.
CPC ............ *B65D 83/752* (2013.01); *A61K 8/046* (2013.01); *A61K 8/33* (2013.01); *A61K 8/731* (2013.01);
(Continued)

(58) Field of Classification Search
CPC ...... B65D 83/752; B65D 83/34; B65D 83/48; B65D 83/20; B65D 83/32; A61K 8/8158;
(Continued)

(56) References Cited

U.S. PATENT DOCUMENTS 3,120,348 A 2/1964 O'Donnell
3,137,416 A 6/1964 Shepherd et al.
(Continued)

FOREIGN PATENT DOCUMENTS

DE 1935991 U 3/1966
DE 3048011 A 7/1982
(Continued)

OTHER PUBLICATIONS

Miao Wang; Acrylates/Hydroxyesters Acrylates Copolymer in Personal Care Applications: Acudyne DHR Durable Hold Resin; RD478006; Feb. 10, 2004.
(Continued)

*Primary Examiner* — Donnell Long
(74) *Attorney, Agent, or Firm* — Alexandra S. Anoff

(57) ABSTRACT

Described herein is an aerosol hairspray product including a container including a container wall which encloses a reservoir. The reservoir includes from about 40% to about 70% of a hairstyling formulation and from about 30% to about 60% of a dimethyl ether propellant. The hairstyling formulation includes water, one or more hairstyling polymers, and from about 0.05% to about 2% alcohol. A spraying device is attached to the container. The spraying devices includes a valve including a valve housing including a vapor tap including a vapor tap area. A dip tube is connected to the valve. The dip tube includes a dip tube orifice including a dip tube orifice area. The ratio of the vapor tap area to the dip tube orifice area is from about 0.005 to about 0.15.

20 Claims, 7 Drawing Sheets

(51) Int. Cl.
*A61K 8/33* (2006.01)
*B65D 83/32* (2006.01)
*B65D 83/20* (2006.01)
*B65D 83/48* (2006.01)
*A61K 8/73* (2006.01)
*A61K 8/81* (2006.01)
*A61K 8/87* (2006.01)
*A61K 8/04* (2006.01)
*B05B 7/04* (2006.01)
*B65D 83/34* (2006.01)

(52) U.S. Cl.
CPC ............ *A61K 8/736* (2013.01); *A61K 8/8147* (2013.01); *A61K 8/8152* (2013.01); *A61K 8/8158* (2013.01); *A61K 8/8182* (2013.01); *A61K 8/87* (2013.01); *A61Q 5/06* (2013.01); *B05B 7/0483* (2013.01); *B65D 83/20* (2013.01); *B65D 83/32* (2013.01); *B65D 83/34* (2013.01); *B65D 83/48* (2013.01); *A61K 2800/30* (2013.01)

(58) Field of Classification Search
CPC ...... A61K 8/8152; A61K 8/731; A61K 8/736; A61K 8/046; A61K 8/8147; A61K 8/87; A61K 8/8182; A61K 8/33; A61K 2800/30; B05B 7/0483; A61Q 5/06
USPC ....................................................... 222/402.1
See application file for complete search history.

(56) References Cited

U.S. PATENT DOCUMENTS

| | | |
|---|---|---|
| 3,146,922 A | 9/1964 | Tuttle |
| 3,472,243 A | 10/1969 | Wall |
| 3,472,604 A | 10/1969 | Dasher |
| 3,475,114 A | 10/1969 | Bolinger |
| 3,537,809 A | 11/1970 | Cednas |
| 3,583,408 A | 6/1971 | Wall |
| 3,587,942 A | 6/1971 | Gailitis |
| 3,619,114 A | 11/1971 | Anzuino |
| 3,619,117 A | 11/1971 | Anzuino |
| 3,619,118 A | 11/1971 | Anzuino |
| 3,633,591 A | 1/1972 | Anzuino |
| 3,634,022 A | 1/1972 | Robbins |
| 3,661,161 A | 5/1972 | Kalopissis |
| 3,676,550 A | 7/1972 | Anzuino |
| 3,678,157 A | 7/1972 | Kalopissis |
| 3,680,738 A | 8/1972 | Vos |
| 3,819,090 A | 6/1974 | Birrell |
| 3,820,550 A | 6/1974 | Kinney |
| 3,876,168 A | 4/1975 | Powers, Jr. |
| 3,882,114 A | 5/1975 | Kalopissis |
| 3,909,195 A | 9/1975 | Machell |
| 4,152,416 A | 5/1979 | Marra |
| 4,167,692 A | 9/1979 | Sekiya et al. |
| 4,257,560 A | 3/1981 | Diamond |
| 4,278,659 A | 7/1981 | Breuer |
| 4,338,295 A | 7/1982 | Highley |
| 4,393,984 A | 7/1983 | Debard |
| 4,417,674 A | 11/1983 | Giuffredi |
| 4,588,760 A | 5/1986 | Jachowicz |
| 4,699,936 A | 10/1987 | Vasta |
| 4,719,104 A | 1/1988 | Patel |
| 4,726,945 A | 2/1988 | Patel |
| 4,801,853 A | 1/1989 | Lewis et al. |
| 4,890,049 A | 12/1989 | Auinger |
| 5,002,761 A | 3/1991 | Mueller |
| 5,068,099 A | 11/1991 | Sramek |
| 5,068,587 A | 11/1991 | Nakamura et al. |
| 5,094,364 A | 3/1992 | Knickerbocker |
| 5,105,988 A | 4/1992 | Knickerbocker |
| 5,126,124 A | 6/1992 | Tazi et al. |
| 5,182,098 A | 1/1993 | Kopolow et al. |
| 5,199,615 A | 4/1993 | Downing |
| 5,207,785 A | 5/1993 | Knickerbocker |
| 5,223,247 A | 6/1993 | Kopolow et al. |
| 5,304,368 A | 4/1994 | Shernov et al. |
| 5,306,972 A | 4/1994 | Hokanson et al. |
| 5,348,731 A | 9/1994 | Patti |
| 5,362,486 A | 11/1994 | Nandagiri |
| 5,385,303 A | 1/1995 | Gosselin |
| 5,411,185 A | 5/1995 | Drobish |
| 5,441,728 A | 8/1995 | Tsaur |
| 5,458,871 A | 10/1995 | Malawer et al. |
| 5,462,727 A | 10/1995 | Engler |
| 5,468,791 A | 11/1995 | Yuan |
| 5,525,657 A | 6/1996 | Anchor et al. |
| 5,526,985 A | 6/1996 | Martin |
| 5,560,544 A | 10/1996 | Merritt |
| 5,614,799 A | 3/1997 | Anderson et al. |
| 5,637,296 A | 6/1997 | Rocafort |
| 5,665,804 A | 9/1997 | Hill |
| 5,676,311 A | 10/1997 | Hartman |
| 5,735,465 A | 4/1998 | LaForcade |
| 5,752,396 A | 5/1998 | Schmid et al. |
| 5,901,907 A | 5/1999 | Hildebrandt |
| 5,912,522 A | 6/1999 | Rivera |
| 5,918,774 A | 7/1999 | Lund |
| 5,927,604 A | 7/1999 | Laidler |
| 6,000,633 A | 12/1999 | Lund |
| 6,106,577 A | 8/2000 | Audousset |
| 6,126,921 A | 10/2000 | Emmerling |
| 6,136,884 A | 10/2000 | Chen |
| 6,158,625 A | 12/2000 | Siegel |
| 6,165,446 A | 12/2000 | Samain |
| 6,215,261 B1 | 4/2001 | Becerra |
| 6,223,951 B1 | 5/2001 | Siegel |
| 6,264,067 B1 | 7/2001 | Lasserre |
| 6,346,234 B1 | 2/2002 | Rollat |
| 6,350,439 B1 | 2/2002 | Dupuis |
| 6,440,404 B1 | 8/2002 | Dupuis |
| 6,482,808 B1 | 11/2002 | Grasser |
| 6,495,119 B1 | 12/2002 | Sturla et al. |
| 6,503,479 B1 | 1/2003 | LesAulnier |
| 6,509,012 B1 | 1/2003 | Hossel |
| 6,512,034 B1 | 1/2003 | Hamada et al. |
| 6,543,703 B2 | 4/2003 | Blake |
| 6,558,697 B2 | 5/2003 | Cannell |
| 6,655,552 B2 | 12/2003 | Aiken |
| 6,727,668 B1 | 4/2004 | Maslov et al. |
| 6,740,317 B1 | 5/2004 | Cho |
| 6,852,815 B1 | 2/2005 | Chuang |
| 6,913,711 B2 | 7/2005 | McKie |
| 6,942,851 B2 * | 9/2005 | Fath .......................... A61K 8/29 424/195.15 |
| 6,966,465 B2 | 11/2005 | Kang |
| 7,014,127 B2 * | 3/2006 | Valpey, III ............ B65D 83/752 222/402.1 |
| 7,028,866 B2 | 4/2006 | Kunesh |
| 7,102,307 B2 | 9/2006 | Shao |
| 7,169,380 B2 | 1/2007 | Rollat |
| 7,205,271 B2 | 4/2007 | Drzewinski |
| 7,255,869 B2 | 8/2007 | Uchida |
| 7,303,087 B2 | 12/2007 | Flashinski |
| 7,364,055 B2 | 4/2008 | Yquel |
| 7,448,517 B2 | 11/2008 | Shieh et al. |
| 7,452,525 B1 | 11/2008 | Berezkin |
| 7,487,891 B2 | 2/2009 | Yerby |
| 7,888,904 B2 | 2/2011 | Mularcik |
| 7,972,589 B2 | 7/2011 | Leighton |
| 7,981,167 B2 | 7/2011 | Carballada |
| 8,048,846 B2 | 11/2011 | Chahal |
| 8,114,938 B2 | 2/2012 | Berezkin |
| D658,009 S | 4/2012 | Davis |
| 8,173,583 B2 | 5/2012 | Castro |
| 8,241,613 B2 | 8/2012 | Candau |
| 8,318,879 B2 | 11/2012 | Hashemzadeh |
| 8,328,120 B2 | 12/2012 | Vanblaere |
| D681,344 S | 5/2013 | McNeill |
| 8,440,211 B2 | 5/2013 | Auguste |
| 8,981,696 B2 | 3/2015 | Bates et al. |

(56) References Cited

U.S. PATENT DOCUMENTS

| | | | |
|---|---|---|---|
| 9,040,024 B2 * | 5/2015 | Tasz | A61L 9/01 424/45 |
| 9,259,481 B2 | 2/2016 | Shin et al. | |
| 9,694,087 B2 | 7/2017 | Shin et al. | |
| 2002/0028187 A1 | 3/2002 | Nekludoff et al. | |
| 2002/0125462 A1 | 9/2002 | McKie et al. | |
| 2002/0150542 A1 | 10/2002 | Steinmetz et al. | |
| 2002/0176834 A1 | 11/2002 | Adams | |
| 2003/0082223 A1 | 5/2003 | Healy et al. | |
| 2003/0103930 A1 | 6/2003 | Uchida | |
| 2003/0106901 A1 | 6/2003 | Meshberg | |
| 2003/0175229 A1 | 9/2003 | Giroud | |
| 2003/0215399 A1 | 11/2003 | Smith | |
| 2003/0215400 A1 | 11/2003 | Schroeder | |
| 2004/0013615 A1 | 1/2004 | Dubief | |
| 2004/0016062 A1 | 1/2004 | Plos | |
| 2004/0042974 A1 | 3/2004 | Dupuis et al. | |
| 2004/0115151 A1 | 6/2004 | Giroud | |
| 2004/0136921 A1 | 7/2004 | Schulz et al. | |
| 2004/0144863 A1 | 7/2004 | Kendrick et al. | |
| 2004/0166071 A1 | 8/2004 | Pfaffernoschke | |
| 2004/0245294 A1 | 12/2004 | Mineau | |
| 2004/0261198 A1 | 12/2004 | Kainz | |
| 2005/0023368 A1 | 2/2005 | Valpey, III et al. | |
| 2005/0052080 A1 | 3/2005 | Maslov et al. | |
| 2006/0060554 A1 | 3/2006 | Garman | |
| 2006/0076171 A1 | 4/2006 | Donnelly et al. | |
| 2006/0105003 A9 | 5/2006 | Rollat-Corvol | |
| 2007/0018017 A1 | 1/2007 | Tilton | |
| 2007/0066506 A1 | 3/2007 | Behler | |
| 2007/0241132 A1 | 10/2007 | Smith | |
| 2007/0245538 A1 | 10/2007 | Salameh | |
| 2007/0267447 A1 | 11/2007 | Kennedy | |
| 2007/0275020 A1 | 11/2007 | Lendlein | |
| 2007/0277332 A1 | 12/2007 | Bimczok | |
| 2007/0286833 A1 | 12/2007 | Keller | |
| 2007/0292641 A1 | 12/2007 | Altonen | |
| 2008/0003387 A1 | 1/2008 | Altonen | |
| 2008/0017666 A1 | 1/2008 | Vanblaere | |
| 2008/0020004 A1 | 1/2008 | Birkel | |
| 2008/0035638 A1 | 2/2008 | Burghaus | |
| 2008/0041884 A1 | 2/2008 | Chevalier | |
| 2008/0102051 A1 | 5/2008 | Huynh | |
| 2008/0112898 A1 | 5/2008 | Schiemann et al. | |
| 2008/0116759 A1 | 5/2008 | Lin | |
| 2008/0152610 A1 | 6/2008 | Cajan et al. | |
| 2008/0166305 A1 | 7/2008 | Singh et al. | |
| 2008/0187505 A1 | 8/2008 | Speckbacher | |
| 2008/0187506 A1 | 8/2008 | Carballada | |
| 2008/0197152 A1 | 8/2008 | Neuhaus | |
| 2008/0210253 A1 | 9/2008 | Carballada | |
| 2008/0219934 A1 | 9/2008 | Kim | |
| 2008/0279804 A1 | 11/2008 | Parker | |
| 2008/0311050 A1 | 12/2008 | Lendlein | |
| 2009/0010865 A1 | 1/2009 | Kim | |
| 2009/0022681 A1 | 1/2009 | Carballada | |
| 2009/0041689 A1 | 2/2009 | Berezkin | |
| 2009/0050599 A1 | 2/2009 | Martin | |
| 2009/0050634 A1 | 2/2009 | Girardot | |
| 2009/0050638 A1 | 2/2009 | Smith | |
| 2009/0060858 A1 | 3/2009 | Schwarzwaelder | |
| 2009/0060859 A1 | 3/2009 | Garcia Castro et al. | |
| 2009/0074697 A1 | 3/2009 | Huynh | |
| 2009/0084870 A1 | 4/2009 | Smith | |
| 2009/0084872 A1 | 4/2009 | Vanblaere | |
| 2009/0104138 A1 | 4/2009 | Shimatani | |
| 2009/0118044 A1 | 5/2009 | Kuo | |
| 2009/0124961 A1 | 5/2009 | Harman | |
| 2009/0160392 A1 | 6/2009 | Mularcik | |
| 2009/0295315 A1 | 12/2009 | Tarnow et al. | |
| 2009/0297467 A1 | 12/2009 | Laurent | |
| 2010/0028286 A1 | 2/2010 | Carballada | |
| 2010/0052584 A1 | 3/2010 | Bates et al. | |
| 2010/0116909 A1 | 5/2010 | Abduljalil | |
| 2010/0123426 A1 | 5/2010 | Nashiki et al. | |
| 2010/0135917 A1 | 6/2010 | Winter | |
| 2010/0189664 A1 | 7/2010 | Castro | |
| 2011/0027211 A1 | 2/2011 | Viala | |
| 2011/0064684 A1 | 3/2011 | Krause | |
| 2011/0114759 A1 | 5/2011 | Schmitz | |
| 2011/0158928 A1 | 6/2011 | Mueller et al. | |
| 2011/0192415 A1 | 8/2011 | Verboom et al. | |
| 2011/0205662 A1 | 8/2011 | Bates et al. | |
| 2011/0241592 A1 | 10/2011 | Lin | |
| 2011/0303766 A1 | 12/2011 | Smith | |
| 2011/0303767 A1 | 12/2011 | Smith | |
| 2012/0031419 A1 | 2/2012 | Batt | |
| 2012/0034173 A1 | 2/2012 | Batt | |
| 2012/0111898 A1 | 5/2012 | Neuhaus | |
| 2012/0180807 A1 | 7/2012 | Flohr | |
| 2012/0183486 A1 | 7/2012 | Flohr | |
| 2012/0263669 A1 | 10/2012 | Mueller et al. | |
| 2013/0058882 A1 | 3/2013 | Flohr | |
| 2013/0068243 A1 | 3/2013 | Birkel | |
| 2013/0068849 A1 | 3/2013 | Birkel | |
| 2014/0070025 A1 | 3/2014 | Dalbo | |
| 2015/0000687 A1 | 1/2015 | Brown | |
| 2015/0004200 A1 | 1/2015 | Brown | |
| 2015/0232260 A1 * | 8/2015 | Dann | B65D 83/752 222/402.1 |
| 2016/0030307 A1 * | 2/2016 | Chen | A61K 8/365 424/70.16 |
| 2016/0175237 A1 * | 6/2016 | Shin | A61K 8/895 424/70.9 |
| 2016/0175238 A1 * | 6/2016 | Shin | A61K 8/895 424/43 |
| 2016/0250120 A1 * | 9/2016 | Knappe | A61K 8/39 |
| 2016/0263009 A1 * | 9/2016 | Saito | A61K 8/8147 |
| 2016/0303023 A1 * | 10/2016 | Bevinakatti | A61K 8/34 |
| 2016/0346175 A1 * | 12/2016 | Sasik | A61Q 5/06 |
| 2016/0347536 A1 | 12/2016 | Brown et al. | |

FOREIGN PATENT DOCUMENTS

| | | |
|---|---|---|
| DE | 4121834 A1 | 1/1993 |
| DE | 4431577 A1 | 3/1996 |
| DE | 29615896 U1 | 1/1998 |
| DE | 10259199 A1 | 6/2004 |
| DE | 102004036004 A1 | 2/2006 |
| DE | 102005018205 A1 | 10/2006 |
| DE | 102008024650 A1 | 4/2010 |
| EP | 0379627 A1 | 8/1990 |
| EP | 0574607 A1 | 12/1993 |
| EP | 0471054 B1 | 5/1994 |
| EP | 0688577 A1 | 12/1995 |
| EP | 0644750 B1 | 4/1996 |
| EP | 0618793 B1 | 5/1997 |
| EP | 0696545 B1 | 6/1999 |
| EP | 1026220 A1 | 8/2000 |
| EP | 0151973 A2 | 7/2001 |
| EP | 0873946 B1 | 7/2001 |
| EP | 0758222 B1 | 8/2001 |
| EP | 0791351 B1 | 12/2002 |
| EP | 1220956 B1 | 7/2003 |
| EP | 0832639 B1 | 1/2004 |
| EP | 1161934 B1 | 4/2004 |
| EP | 1092650 B1 | 12/2005 |
| EP | 1160178 B1 | 7/2006 |
| EP | 1681078 B1 | 12/2008 |
| EP | 1719500 B1 | 6/2010 |
| EP | 2407145 A1 | 1/2012 |
| EP | 2228319 B1 | 5/2013 |
| FR | 2784081 B1 | 4/2000 |
| JP | H0454116 A | 2/1992 |
| JP | H04208214 A | 7/1992 |
| JP | H10279436 A | 10/1998 |
| JP | 10337509 A | 12/1998 |
| JP | 11076881 A | 3/1999 |
| JP | 11228398 A * | 8/1999 |
| JP | 2001227475 A | 8/2001 |
| JP | 2002347866 A | 12/2002 |
| JP | 2003054668 A | 2/2003 |
| JP | 2004195287 | 7/2004 |

(56) References Cited

FOREIGN PATENT DOCUMENTS

| | | |
|---|---|---|
| JP | 3727112 B2 | 12/2005 |
| JP | 3828257 B2 | 10/2006 |
| JP | 2007117940 A | 5/2007 |
| JP | 3969517 B2 | 9/2007 |
| JP | 2007296428 A | 11/2007 |
| JP | 4278878 B2 | 6/2009 |
| JP | 2011-190195 A | 9/2011 |
| WO | WO9725259 A1 | 7/1997 |
| WO | WO9729029 A1 | 8/1997 |
| WO | WO9800354 A1 | 1/1998 |
| WO | WO9967216 A1 | 12/1999 |
| WO | WO200045777 A1 | 8/2000 |
| WO | WO200153157 A2 | 7/2001 |
| WO | WO0170179 A1 | 9/2001 |
| WO | WO200213773 A2 | 2/2002 |
| WO | WO200245665 A1 | 6/2002 |
| WO | WO03061839 A1 | 7/2003 |
| WO | WO2004043330 A2 | 5/2004 |
| WO | WO2004062633 A1 | 7/2004 |
| WO | WO2007099268 A2 | 9/2007 |
| WO | WO2007099269 A2 | 9/2007 |
| WO | WO2007099271 A2 | 9/2007 |
| WO | WO2012009302 A1 | 1/2012 |

OTHER PUBLICATIONS

Andrea Keenan; Hair Styling Formulations Containing Acudyne 180 Hair Fixative Polymer and Aculyn Rheology Modifiers; RD478088; Feb. 10, 2004.

Miao Wang; Mousse Formulations Containing Acudyne DHR or Acudyne 180 Hair Fixative Polymer and Aculyn 88 Rheology Modifier; RD510027; Oct. 10, 2006.

PCT International Search Report and Written Opinion for PCT/US2016/035210 dated Jul. 28, 2016, 13 pages.

"The Shellac Story—Shellac Properties", retrieved from the internet: http://www.shellac.in.shellac_properties.html, retrieved on Jul. 11, 2016.

All final and non-final office actions for U.S. Appl. No. 13/180,931.
All final and non-final office actions for U.S. Appl. No. 13/181,058.
All final and non-final office actions for U.S. Appl. No. 13/614,249.
All final and non-final office actions for U.S. Appl. No. 13/614,925.
All final and non-final office actions for U.S. Appl. No. 14/315,917.
All final and non-final office actions for U.S. Appl. No. 14/315,950.
CAS Registry entry for 1,2-difluoroethane, 2014.
CAS Registry entry for dimethyl ether, 2014.
PCT International Search Report and Written Opinion for PCT/US2014/044332 dated Dec. 23, 2014, 10 pages.
PCT International Search Report and Written Opinion for PCT/US2014/044339 dated Jan. 22, 2015, 14 pages.
Philip M. Cook; Low VOC Hairsprays—It Depends Very Much on the Choice of Polymer—XP009146664 Extended EPSR.
Product introduction: inserts [online], by Precision Valve Japan, Ltd, 2006 [Searching date: Jun. 22, 2016] <URL: http://pvj.co.jp/Iv2/index.php?>.
Troy, Remington: The Science and Practice of Pharmacy Baltimore: Lipponcott Williams & Wilkins, 2006, p. 1009 (Year: 2006).

* cited by examiner

Fig. 6

A 60C/40P ratio at a lower concentrate viscosity within the desired VT/DT area range, results in target delivery, no clogging, and smallest overall Dv50 and Dv90 droplet size through the life of the can

- 50/50 Visc 5 DV50 (Tabel 5 - Formula E)
- 50/50 Visc. 5 Dv90 (Tabel 5 - Formula E)
- 60/40 Visc. 5 Dv50 (Table 5 - Formula F)
- 60/40 Visc. 5 Dv90 (Table 5 - Formula F)
- 60/40 Visc. 4 Dv50 (Table 5 - Formula H)
- 60/40 Visc. 4 Dv90 (Table 5 - Formula H)

X-axis: % of total can contents left
Y-axis: Dv50 and Dv 90 Droplet Size, μm

Fig. 7

Within desired VT/DT area optimizing fill ratio and viscosity results in all Category 1 sprays and removes spray cut-off sputtering

[Bar chart: % of cans tested, Clog type results (y-axis, 0–100) vs. two conditions on x-axis: "50C/50P Fill, viscosity 5cst concentrate (Table 5 – Formula A)" showing ~40% Partial Clog and ~60% No Clog; "60C/40P Fill, viscosity 4cst concentrate (Table 5 – Formula H)" showing 100% No Clog. Legend: Partial Clog, No Clog.]

AEROSOL HAIRSPRAY PRODUCT COMPRISING A SPRAYING DEVICE

FIELD OF THE INVENTION

Described herein is an aerosol hairspray product that is substantially free of ethanol, includes a dimethyl ether propellant, and has a ratio of the vapor tap area to the dip tube area of from about 0.0005 to about 0.15.

BACKGROUND OF THE INVENTION

Hairstyling products such as hairsprays are used for achieving different hairstyles and for holding hair strands in place for a period of time. Typically, hairsprays comprise film-forming polymers, which when applied to keratin-containing fibres, such as human hair, form fibre-fibre welds. These welds 'glue' the fibres together and hence impart hold to the hairstyle.

Aerosol hairspray products usually comprise a pressure-resistant container, a nozzle, a propellant, and a hairstyling formulation. A hairspray composition is normally ejected from such products via aerosol-forming nozzle. Alcohols are normally used in the hairstyling formulation, for example to reduce surface tension. However, a high proportion of alcohol may leave the hair feeling dry and brittle and some alcohols may cause an allergic response in some users. In addition, ethanol is a volatile organic compound which may accumulate in the environment and cause environmental concerns. Also, ethanol is flammable.

There is a constant need, therefore, for more environmentally friendly, more sustainable, less harsh, and more affordable hairspray products. However, altering one or more features of an aerosol hairspray product can be challenging since the interrelationship therebetween affects the product performance. For example, utilising a different propellant or a different spraying device may result in an unacceptable decrease in package operating pressure resulting in an increased product wetness on application, or may result in unwanted clogging.

Based on the foregoing, there is a need for an aerosol hairspray product that is substantially free of ethanol, provides acceptable or superior product performance, and has a low propensity to clog.

SUMMARY OF THE INVENTION

Described herein is an aerosol hairspray product wherein the aerosol hairspray product comprises (a) a container (100) comprising a container wall (110) which encloses a reservoir (120), wherein the reservoir (120) comprises from about 40% to about 70% of a hairstyling formulation and from about 30% to about 60% of a dimethyl ether propellant, by total weight of the hairstyling formulation and the dimethyl ether propellant; (b) wherein the hairstyling formulation comprises (1) from about 30% to about 60% water, by total weight of the hairstyling formulation and the dimethyl ether propellant; (2) from about 5% to about 15% of one or more hairstyling polymers by total weight of the hairstyling formulation and the dimethyl ether propellant, wherein the hairstyling polymer is water-soluble and has a molecular weight of less than 200,000 g/mol; (3) from about 0.05% to about 2% alcohol, by total weight of the hairstyling formulation and the dimethyl ether propellant; and (4) is substantially free of ethanol; wherein the hairstyling formulation has a viscosity of from about 2.5 cSt to about 5.5 cSt; (c) a spraying device (200) attached to the container (100) for dispensing the hairstyling formulation from the reservoir (120) of the container (100); wherein the spraying device (200) is fluidly connected to the reservoir (120); wherein the spraying device (200) comprises a spray actuator (150) and a valve (130); wherein the valve (130) comprises a valve housing (140); wherein the valve housing (140) comprises a vapor tap (160); wherein the vapor tap (160) comprises a vapor tap area; wherein a dip tube (170) is fluidly connected to the valve (130); wherein the dip tube (170) comprises a dip tube orifice (175); wherein the dip tube orifice (175) comprises a dip tube orifice area; and wherein the ratio of the vapor tap area to the dip tube orifice area is from about 0.005 to about 0.15.

Also described herein is an aerosol hairspray product wherein the aerosol hairspray product comprises (a) a container (100) comprising a container wall (110) which encloses a reservoir (120), wherein the reservoir (120) comprises from about 40% to about 70% of a hairstyling formulation and from about 35% to about 55% of a dimethyl ether propellant, by total weight of the hairstyling formulation and the dimethyl ether propellant; (b) wherein the hairstyling formulation comprises (1) from about 35% to about 60% water, by total weight of the hairstyling formulation and the dimethyl ether propellant; (2) from about 5% to about 8% of one or more hairstyling polymers by total weight of the hairstyling formulation and the dimethyl ether propellant, wherein the one or more hairstyling polymers is water-soluble and has a molecular weight of less than 200,000 g/mol, wherein the one or more hairstyling polymers comprises an acrylate based system that comprises at least one monomer of acrylic acid or methacrylic acid, at least one ester of an acrylate, and a polyurethane; (3) from about 0.05% to about 2% alcohol, by total weight of the hairstyling formulation and the dimethyl ether propellant; and (4) is substantially free of ethanol; wherein the hairstyling formulation has a viscosity of from about 3 cSt to about 5 cSt; (c) a spraying device (200) attached to the container (100) for dispensing the hairstyling formulation from the reservoir (120) of the container (100); wherein the spraying device (200) is fluidly connected to the reservoir (120); wherein the spraying device (200) comprises a spray actuator (150) and a valve (130); wherein the valve (130) comprises a valve housing (140); wherein the valve housing (140) comprises a vapor tap (160); wherein the vapor tap (160) comprises a vapor tap area; wherein a dip tube (170) is fluidly connected to the valve (130); wherein the dip tube (170) comprises a dip tube orifice (175); wherein the dip tube orifice (175) comprises a dip tube orifice area; wherein the ratio of the vapor tap area to the dip tube orifice area is from about 0.008 to about 0.09; and wherein the valve housing does not comprise two or more vapor taps.

Also described herein is a hairstyling method comprising (a) providing an aerosol hairspray product comprising (1) a container (100) comprising a container wall (110) which encloses a reservoir (120), wherein the reservoir (120) comprises from about 40% to about 70% of a hairstyling formulation and from about 30% to about 60% of a dimethyl ether propellant, by total weight of the hairstyling formulation and the dimethyl ether propellant; (2) wherein the hairstyling formulation comprises (i) from about 30% to about 60% water, by total weight of the hairstyling formulation and the dimethyl ether propellant; (ii) from about 5% to about 15% of one or more hairstyling polymers by total weight of the hairstyling formulation and the dimethyl ether propellant, wherein the hairstyling polymer is water-soluble and has a molecular weight of less than 200,000 g/mol; (iii) from about 0.05% to about 2% alcohol, by total weight of the hairstyling formulation and the dimethyl ether propellant; and (iv) is substantially free of ethanol; wherein the hairstyling formulation has a viscosity of from about 2.5 cSt to about 5.5 cSt; (3) a spraying device (200) attached to the container (100) for dispensing the hairstyling formulation from the reservoir (120) of the container (100); wherein the spraying device (200) is fluidly connected to the reservoir (120); wherein the spraying device (200) comprises a spray actuator (150) and a valve (130); wherein the valve (130) comprises a valve housing (140); wherein the valve housing (140) comprises a vapor tap (160); wherein the vapor tap (160) comprises a vapor tap area; wherein a dip tube (170) is fluidly connected to the valve (130); wherein the dip tube (170) comprises a dip tube orifice (175); wherein the dip tube orifice (175) comprises a dip tube orifice area; and wherein the ratio of the vapor tap area to the dip tube orifice area is from about 0.005 to about 0.15; and (c) causing the aerosol hairspray product to spray at a delivery rate, wherein the delivery rate is from about 0.30 g/sec to about 0.50 g/sec; and wherein an ejected composition is sprayed, wherein the ejected composition comprises particles having a Dv50 droplet size of from about 40 micron to about 100 micron and a Dv90 droplet size of from about 160 micron to about 300 micron.

BRIEF DESCRIPTION OF THE DRAWINGS

While the specification concludes with the claims particularly pointing out and distinctly claiming the invention, it is believed that the aerosol hairspray product described herein will be better understood from the following description taken in conjunction with the accompanying drawings in which:

FIG. 6 is a line graph showing droplet size distributions at different VT/DT area ratios.

FIG. 7 is a bar graph showing cut-off sputter/spray deformities at different concentrate viscosities.

DETAILED DESCRIPTION OF THE INVENTION

Figure 1:
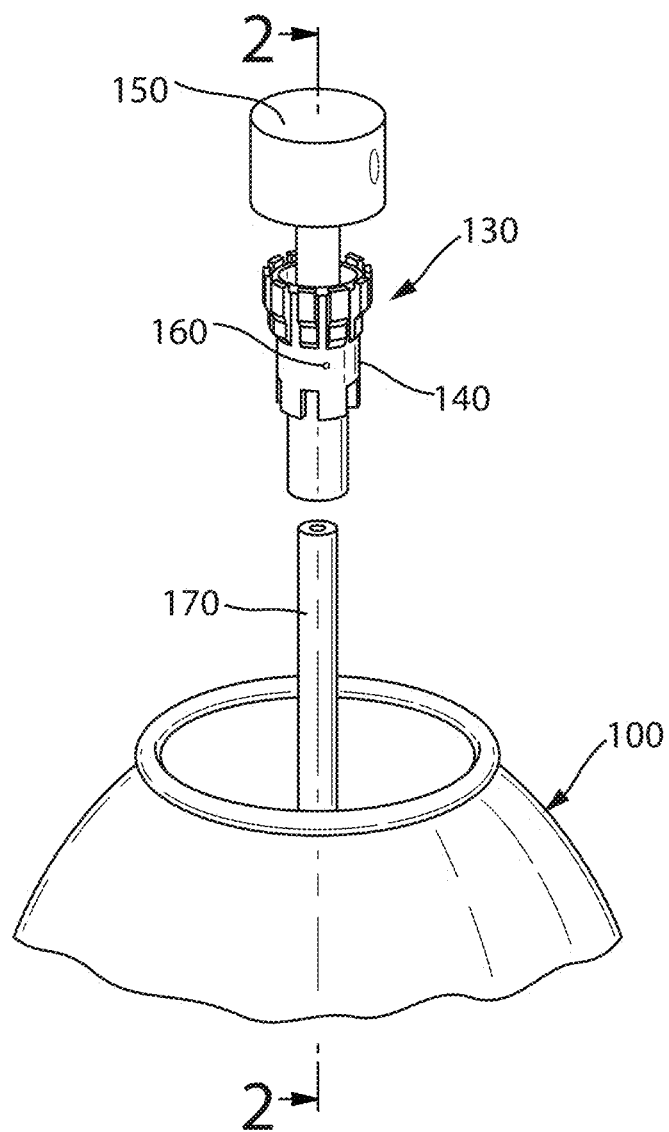
FIG. 1 is an exploded view of a spraying device.
Figure 2:
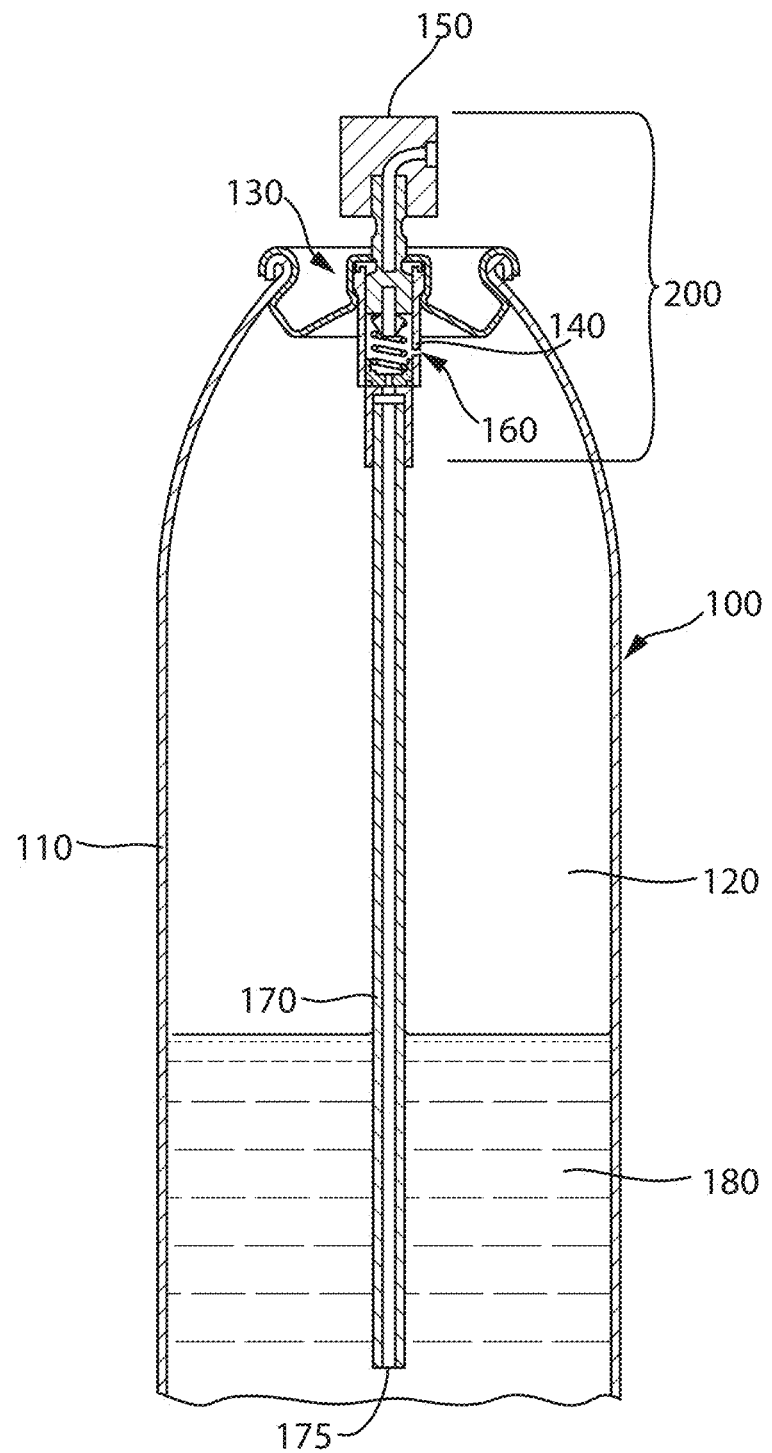
FIG. 2 is a cross-section view of an aerosol hairspray product.

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

The term "comprising," as used herein, means that other steps and other ingredients which do not affect the end result can be added. This term encompasses the terms "consisting of" and "consisting essentially of." The compositions and methods/processes of the present invention can comprise, consist of, and consist essentially of the elements and limitations of the invention described herein, as well as any of the additional or optional ingredients, components, steps, or limitations described herein.

The terms "include," "includes," and "including," as used herein, are meant to be non-limiting and are understood to mean "comprise," "comprises," and "comprising," respectively.

Where amount ranges are given, these normally relate to the total amount of the (class of) compound(s) specified. For example, "the composition comprises from about 0.1% to about 20% of ethylenic monomer" means that the total amount of ethylenic monomer (including mixtures of different such monomers) in the composition must be within the specified range.

The term "substantially free," as used herein, means less than about 1%, alternatively less than about 0.8%, alternatively less than about 0.5%, alternatively less than about 0.3%, or alternatively about 0%, by total weight of the hair styling formulation and the dimethyl ether propellant.

"Hair," as used herein, means mammalian hair including scalp hair, facial hair and body hair, more preferably hair on the human head and scalp. "Hair shaft" means an individual hair strand and may be used interchangeably with the term "hair."

"Cosmetically acceptable," as used herein, means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives," as used herein, includes but is not limited to, amide, ether, ester, amino, carboxyl, acetyl, acid, salt and/or alcohol derivatives of a given compound.

"Monomer," as used herein, means a discrete, non-polymerised chemical moiety capable of undergoing polymerisation in the presence of an initiator. "Ethylenic monomer," as used herein, means a chemical species that contains an olefinic carbon-carbon double bond (C=C) and is capable of undergoing polymerization in the presence of an initiator.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. A polymer comprises at least two monomers. Polymers made from two or more different types of monomers are called copolymers. The distribution of the different monomers can be calculated statistically or block-wise—both possibilities are suitable for the present invention. Except if stated otherwise, the term "polymer" used herein includes any type of polymer including homopolymers and copolymers.

The term "water-soluble" as used herein refers to any material that is sufficiently soluble in water to form a single-phase solution to the naked eye at a concentration of 0.1% by weight of the material in water at 25° C. It may be necessary to adjust the pH of the mixture or fully neutralize the mixture after addition of the material to water to achieve the water solubility. These methods are well-known, for example, in the water-soluble hairstyling polymer applications industry and are typically instructed with the supplied material sample. Water-solubility is typically measured by the following protocol: 0.1% by weight of the material is added to distilled water at 25° C. and the pH adjusted/neutraliser added as needed. This is stirred vigorously on a magnetic stirrer set at 600 rpm, for 30 minutes. The solution is then allowed to settle for 1 hour and the number of phases observed by the naked eye. For example, where any solid material can be seen in an otherwise single-phase solution, then this is considered to be two phases.

The term "water-insoluble" as used herein refers to any material that is not "water-soluble".

The term "molecular weight" or "M.Wt." as used herein refers to the number average molecular weight unless otherwise stated.

"Kit," as used herein, means a packaging unit comprising a plurality of components i.e. a kit of parts. An example of a kit is, for example, a first composition and a separately packaged second composition. Another kit may comprise application instructions comprising a method and a composition/formulation.

Embodiments and aspects described herein may comprise or be combinable with elements or components of other embodiments and/or aspects despite not being expressly exemplified in combination, unless otherwise stated or an incompatibility is stated.

Aerosol Hairspray Product

Described herein is an aerosol hairspray product. The aerosol hairspray product comprises a container (100) comprising a container wall (110) which encloses a reservoir (120) comprising a hairstyling formulation and a dimethyl ether propellant. The reservoir comprises from about 40% to about 70%, alternatively from about 45% to about 65%, alternatively from about 45% to about 60% of the hairstyling formulation, by total weight of the hairstyling formulation and the dimethyl ether propellant. The reservoir comprises from about 30% to about 60%, alternatively from about 35% to about 55%, alternatively from about 40% to about 50% of the dimethyl ether propellant, by total weight of the hairstyling formulation and the dimethyl ether propellant.

In an embodiment, the product is an aerosol hairspray product and thus does not include mousse products or any pump spray products.

Viscosity

In an embodiment, the hairstyling formulation without propellant has a kinematic viscosity of from about 2.5 cSt to about 5.5 cSt, alternatively from about 3 cSt to about 5 cSt, alternatively from about 3.5 cSt to about 4.5 cSt. The kinematic viscosity is measured at 20° C.+/−0.1° C. The kinematic viscosity may be important because when the hairstyling formulation is too viscous then the hairstyling formulation is too thick and cannot be sprayed and/or is clogging—non-homogeneous ejected composition results e.g. irregular spray beam, "spitting" rather than spraying, and/or ejection of lumps.

Kinematic viscosity may be measured by Ubbelohde tube. Kinematic viscosity is a measure of the resistance to flow of a fluid, equal to its absolute viscosity divided by its density. The SI unit of kinematic viscosity is $m^2 \cdot s^{-1}$. The cgs (centimeters/grams/seconds) physical unit for kinematic viscosity is the stokes (St), which can be expressed in terms of centistokes (cSt). 1 cSt=1 $mm^2 \cdot s^{-1} = 10^{-6}$ $m^2 \cdot s^{-1}$. Water at 20° C. has a kinematic viscosity of about 1 cSt. A Ubbelohde tube is a viscometer for measurement of kinematic viscosity of transparent Newtonian liquids by suspended level principle as described in ASTM D 445 and D 446, and ISO 3104 and 3105. For the Ubbelohde tube measure, there is no temperature effect on results, for other kinematic viscometers, temperatures different from specified test range can affect result. Herein, measurements were taken at a temperature of 20° C.+/−0.1° C. This method can be used to measure from about 0.6 cSt to 100 cSt. For instructions for the use of the Ubbelohde viscometer see ASTM D 445. Use Ubbelohde tube size 0 C for viscosities from 0.6 to 3 cSt at 20° C.+/−0.1° C. Use Ubbelohde tube size 1 for viscosities from 2 to 10 cSt at 20° C.+/−0.1° C. ASTM D445 is the "Standard Test Method for Kinematic Viscosity of Transparent and Opaque Liquids". ASTM D446 is "Specifications and Operating Instructions for Glass Capillary Kinematic Viscometers".

Delivery Rate

In an embodiment, the aerosol hairspray product is for spraying at a delivery rate, wherein the delivery rate is from about 0.30 g/sec to about 0.50 g/sec, alternatively from about 0.35 g/sec to about 0.50 g/sec. The delivery rate of may be determined following ASTM D 3069-94, "Standard Test Method for Delivery Rate of Aerosol Products." In this test, the delivery rate of the product is determined by measuring the mass lost in a given time period. This correlates with the quantity of material expelled though the valve and actuator combination in a given time period. In this case, the can is tested at room temperature (at 21° C.) and a duration of 2 sec to 10 sec for the actuation time. The delivery rate is then determined by the equation:

Delivery Rate (g/sec)=Mass loss (g)/Actuation time (sec)

If the delivery rate is greater than about 0.45 g/sec, then the on-hair drying time may be too long for consumer satisfaction. This is unique for the water-based hairsprays described herein as compared to traditional alcohol-based hairsprays, typically traditional hairsprays containing volatile alcohol have delivery rates between about 0.55 g/sec to 0.85 g/sec. Delivery rate can typically be adjusted by altering the pressure inside the container (increased pressure correlates with faster delivery rate) and/or the orifices in the spraying device, such as the orifices in the nozzle, orifices in the valve, and the inner diameter of the diptube.

Particle Size Distribution

In an embodiment, the aerosol hairspray product is for spraying an ejected composition wherein the ejected composition consists of particles having an average particle size distribution (Dv50) of from 40 micron to 100 micron, alternatively from about 45 to about 95 micron, alternatively from about 50 micron to about 90 micron. In an embodiment, the aerosol hairspray product is for spraying an ejected composition wherein the ejected composition consists of particles having an average particle size distribution (Dv90) of from 160 micron to 300 micron, alternatively from about 165 micron to about 295 micron, and alternatively from about 170 micron to about 290 micron.

The droplet size through the life of the can may be important as it impacts the dry feel, dry time and hold performance of the hairspray. Smaller droplets dry faster. More small droplets feel less wet than fewer large droplets. For hold, a larger number of smaller droplets give more surface area coverage to provide an even coating of hair welds. If the droplets are too small they will not bridge hair together in weld points and won't hold. This may be important for alcohol-free hairsprays that do not have the fast evaporation drying advantage of ethanol formulas. Ethanol hairsprays have a much broader working droplet size range i.e. 30-130 um Dv50. An ethanol-free hairspray below 40 um Dv50 may have holding problems. An ethanol-free hairspray above ~80 um Dv50 may have a noticeably slow drying time and initial wet hair feel. The Dv90 represents, though much fewer, the largest droplets in the spray. Dv90's over 180 um that get larger, up to 400 um, over the life of the can may result in sprays that appear visually uneven, with larger and sputtering droplets. These large drops make the spray less misty and even. This may result in clumping of hair where those large drops land. These hair clumps may make the end finished hair results have an unnatural hair feel that is difficult to run fingers or a brush through.

The average particle size distribution (Dv50) may be important in view of ejected composition drying time, which must be consumer acceptable. Indeed, a smaller average particle size distribution (Dv50) may be useful in that more particles have a higher surface area to volume ratio, which means a faster drying time. On the other hand, a too low average particle size distribution (Dv50) may mean that not enough hairstyling polymer is provided to the hair to provide spot welds.

A Malvern Spraytec instrument is used to measure the particle size distribution. The Dv50 is the term to describe the maximum particle size diameter below which 50% of the sample volume possesses, also known as the median particle size by volume. The Dv90 is the term to describe the maximum particle size diameter below which 90% of the sample volume possesses. The Malvern Spraytec instrument uses the technique of laser diffraction for measurement of the size of the spray particles. The intensity of light scattered as a laser beam passes through a spray is measured. This data is then analysed to calculate the size of the particles that created the scattering pattern. A Malvern Spraytec 2000 is used according to the manufacturer's instructions. Test samples have a temperature between 20° C. to 22° C.

Alcohol

The hairstyling formulation comprises from about 0.05% to about 2%, alternatively from about 0.06% to about 1.9%, alternatively from about 0.08% to about 1.7% alcohol, by total weight of the hairstyling formulation and the dimethyl ether propellant. The hairstyling formulation is substantially free of ethanol or comprises 0% ethanol.

Water

The hairstyling formulation comprises from about 30% to about 60%, alternatively from about 35% to about 60%, alternatively from about 39% to about 55%, and alternatively from about 41% to about 50% water by total weight of the hairstyling formulation and the dimethyl ether propellant.

The water may be important because it provides a solvent for the hairstyling polymer and other ingredients in the hairstyling formulation. Water has the advantage that it is readily available, highly affordable, sustainable and environmentally friendly. For example, water is not a VOC. Furthermore, many useful ingredients for the hairstyling formulation dissolve in water i.e. are water soluble, which is another advantage.

Hairstyling Polymer

The hairstyling formulation comprises from about 5% to about 15%, alternatively from about 5% to about 8%, and alternatively from about 5.8% to about 7.4% of one or more hairstyling polymers, by total weight of the hairstyling formulation and the dimethyl ether propellant. In an embodiment, the one or more hairstyling polymers is water-soluble and has a molecular weight of less than 200,000 g/mol.

The amount of the one or more hairstyling polymers may be important in balancing hold performance and on-hair wetness. The amount of hairstyling polymer may drive the hold performance, but may be limited by a maximum sprayable viscosity.

In an embodiment, the one or more hairstyling polymers comprises an acrylate based system that contains at least one monomer of acrylic acid or methacrylic acid, and at least one ester of an acrylate. In an embodiment, the one or more hairstyling polymers comprises an acrylate based system that contains at least one monomer of acrylic acid or methacrylic acid, at least one ester of an acrylate, and a polyurethane.

The one or more hairstyling polymers may be water-soluble hairstyling polymer. The water-based hairstyling formulation of hairstyling polymer(s) may be pressurized in a container (100) with a liquefied gas propellant. When the pressure is released, the liquid boils carrying with it the water and hairstyling polymer(s) plus any optional ingredients. Therefore a homogeneous mixture of the hairspray formulation and the liquefied gas propellant in the pressurized can is desired for a homogeneous ejected composition to be delivered to the hair when the product is sprayed. Homogeneity can happen immediately or over a period of time after the can is pressurized. This can also be achieved by shaking the can prior to spraying the product. For example, it is common in other aerosol products (such as mousses) for the propellant to be insoluble with the rest of the formulation in the can. The one or more hairstyling polymers may be selected based on their ability to form a homogenous mixture when mixed with water and liquefied gas propellant in the pressurized can.

In an embodiment, the one or more hairstyling polymers may be selected from hairstyling polymers forming a homogeneous mixture with water and liquefied gas propellant. In an embodiment, the one or more hairstyling polymers may be selected from hairstyling polymers forming a homogeneous mixture with water and a dimethyl ether propellant. By "homogeneous mixture" herein means a mixture having a single phase, therefore components of the homogeneous mixture have the same proportions throughout the mixture.

The hairstyling polymers may be any water-soluble film-forming polymer or mixture of such polymers. This includes homopolymers or copolymers of natural or synthetic origin having functionality rendering the polymers water-soluble such as hydroxyl, amine, amide or carboxyl groups.

In an embodiment, the water-soluble hairstyling polymers when diluted in water at the range claimed form transparent or semi-transparent stable solutions. Depending on the specific polymer type, it may be necessary to adjust the pH of the formulation or to neutralize the formulation after addition of the polymer to water to achieve water solubility. These methods are well-known in the water soluble polymer applications industry and are typically instructed with the supplied polymer sample. The hairstyling polymer may be classified into two types, (totally) synthetic polymers and natural products together with their chemically modified derivatives and further can be grouped into three main headings; naturally occurring, semi-synthetic and completely synthetic polymers. In at least one embodiment, the hairstyling polymer is selected from the group consisting of: cationic hairstyling polymers, anionic hairstyling polymers, nonionic hairstyling polymers, and amphoteric hairstyling polymers. The molecular weight of the hairstyling polymers may be such that the hairstyling formulation without propellant meets the viscosity requirement range specified. In at least one embodiment, the hairstyling polymers are linear or branched.

In an embodiment, the hairstyling polymer is a cationic hairstyling polymer or a mixture of cationic hairstyling polymers. In at least one embodiment, the cationic hairstyling polymer is selected from the group consisting of: quaternized acrylates or methacrylates; quaternary homopolymers or copolymers of vinylimidazole; homopolymers or copolymers comprising a quaternary dimethdiallyl ammonium chloride; non-cellulosic cationic polysaccharides; cationic cellulose derivatives; chitosans and derivatives thereof; and mixtures thereof.

In an embodiment, the cationic hairstyling polymer may be selected from quaternized acrylates or methacrylates. In at least one embodiment, the cationic hairstyling polymer is a copolymer comprising: a) at least one of: quaternized dialkylaminoalkyl acrylamides (e.g. Quaternized dimethyl amino propyl methacrylamide); or quaternized dialkylaminoalkyl acrylates (e.g. quaternized dimethyl aminoethyl methacrylate) and b) one or more monomers selected from the group consisting of: vinyllactams such as vinylpyrrolidone or vinylcaprolactam; acrylamides, methacrylamides which may or may not be substituted on the nitrogen by lower alkyl groups (C1-C4) (e.g. N-tertbutylacrylamide); esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; and allyl esters or methallyl esters. The counter ion can be either a methosulfate anion or a halide such as chloride or bromide.

In an embodiment, the cationic hairstyling polymer may be a quaternary homopolymer or copolymer of vinylimidazole. In at least one embodiment, the cationic hairstyling polymer is a copolymer comprising a) a quaternized vinylimizazole and b) one or more other monomers. The other monomer may be selected from the group consisting of: vinyllactams such as vinylpyrrolidone or vinylcaprolactam such as vinylpyrrolidone/quaternized vinylimidazole (PQ-16) such as that sold as Luviquat FC-550 by BASF; acrylamides, methacrylamides which may or may not be substituted on the nitrogen by lower alkyl groups (C1-C4) (e.g. N-tertbutylacrylamide); esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. The counter ion can be either a methosulfate anion or a halide such as chloride or bromide.

In an embodiment, the cationic hairstyling polymer may be a dimethdiallyl ammonium chloride. In an embodiment, the cationic hairstyling polymer may be a homopolymer or copolymer comprising a quaternary dimethdiallyl ammonium chloride and another monomer. Such other monomer may be selected from the group consisting of: acrylamides, methacrylamides which may or may not be substituted on the nitrogen by lower alkyl groups (C1-C4) (e.g. N-tertbutylacrylamide); vinyllactams such as vinylpyrrolidone or vinylcaprolactam; esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. The counter ion can be either a methosulfate anion or a halide such as chloride or bromide.

In an embodiment, the cationic hairstyling polymer is a non-cellulosic cationic polysaccharide. In at least one embodiment, the cationic hairstyling polymer is a guar gums such as those containing trialkylammonium cationic groups. For example, such as guar hydroxypropyltrimonium chloride, which is available as N-Hance 3269 from Ashland.

In an embodiment, the cationic hairstyling polymer is a cationic cellulose derivative. In at least one embodiment, the cationic hairstyling polymer is a copolymers of cellulose derivatives such as hydroxyalkylcelluloses (e.g. hydroxymethyl-, hydroxyethyl- or hydroxypropylcelluloses) grafted with a water-soluble monomer comprising a quaternary ammonium (e.g. glycidytrimethyl ammonium, methacryloyloxyethyltrimethylammonium, or a methacrylamidopropyltrimethylammonium, or dimethyldiallylammonium salt). For example, such as hydroxyethylcellulose dimethyldiallyammonium chloride [PQ4] sold as Celquat L200 by Akzo Nobel, or such as Quaternized hydroxyethylcellulose [PQ10] sold as UCARE JR125 by Dow Personal Care.

In an embodiment, the cationic hairstyling polymer is selected from chitosans and derivatives thereof. A derivative of a chitosan includes salts of chitosans. The salts can be chitosan acetate, lactate, glutamate, gluconate or pyrrolidonecarboxylate preferably with a degree of hydrolysis of at least 80%. A suitable chitosan includes Hydagen HCMF by Cognis.

In an embodiment, the hairstyling polymer is an anionic hairstyling polymer or a mixture of anionic hairstyling polymers. In at least one embodiment, the anionic hairstyling polymer is selected from those comprising groups derived from carboxylic or sulfonic acids. Copolymers containing acid units are generally used in their partially or totally neutralized form, more preferably totally neutralized. In at least one embodiment, the anionic hairstyling polymer comprises: (a) at least one monomer derived from a carboxylic acid such as acrylic acid, or methacrylic acid or crotonic acid or their salts, or C4-C8 monounsaturated polycarboxylic acids or anhydrides (e.g. maleic, furamic, itaconic acids and their anhydrides) and (b) one or more monomers selected from the group consisting of: esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly (ethyleneglycol)acrylate); hydroxyesters acrylate (e.g. hydroxyethyl methacrylate); acrylamides, methacrylamides which may or may not be substituted on the nitrogen by lower alkyl groups (C1-C4); N-alkylated acrylamide (e.g. N-tertbutylacrylamide); hydroxyalkylated acrylamide; amino alkylated acrylamide (e.g. dimethyl amino propyl methacrylamide); alkylacrylamine (e.g. tert-butylaminoethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters; vinyllactams such as vinylpyrrolidone or vinylcapro lactam; alkyl maleimide, hydroxyalkyl maleimide (e.g. Ethyl/Ethanol Maleimide). When present the anhydride functions of these polymers can optionally be monoesterified or monoamidated. In at least one embodiment, the anionic hairstyling polymer comprises monomers derived from a sulfonic acid. In at least one embodiment, anionic polymers comprise: (a) at least one monomer derived from a sulfonic acid such as vinylsulfonic, styrenesulfonic, naphthalenesulfonic, acrylalkyl sulfonic, acrylamidoalkylsulfonic acid or their salts and (b) one or more monomers selected from the group consisting of: esters of acrylic acid and/or methacrylic acid (e.g. C1-C4 alkyl acrylate, methyl acrylate, ethyl acrylate, tertbutyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); acrylamides, methacrylamides which may or may not be substituted on the nitrogen by lower alkyl groups (C1-C4); N-alkylated acrylamide (e.g. N-tertbutylacrylamide); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters; vinyllactams such as vinylpyrrolidone or vinylcapro lactam; alkyl maleimide, hydroxyalkyl maleimide (e.g. Ethyl/Ethanol Maleimide). When present the anhydride functions of these polymers can optionally be monoesterified or monoamidated.

In an embodiment, the anionic hairstyling polymer is a water-soluble polyurethane.

In an embodiment, the anionic hairstyling polymers are advantageously selected from: copolymers derived from acrylic acid such as the acrylic acid/ethylacrylate/N-tert-butylacrylamide terpolymer such as that sold as Ultrahold 8 by BASF; Octylacrylamide/Acrylates/Butylaminoethyl/ Methacrylate Copolymer such as that sold as Amphomer by Akzo Nobel; methacrylic acid/ester acrylate/ester methacrylate such as that sold as Balance CR by Akzo Nobel; Octylacrylamide/Acrylates/Butylaminoethyl Methacrylate Copolymer such as that sold as Balance 47 by Akzo nobel; methacrylic acid/hydroxyethylmethacrylate/various acrylate esters such that known as Acudyne 1000 sold by Dow Chemical; acrylates/hydroxyethylmethacrylate such as that sold as Acudyne 180 by Dow Chemical; methacrylic acid/ hydroxyethylmethacrylate/various acrylate esters such as that sold as Acudyne DHR by Dow Chemical; n-butyl methacrylate/methacrylic acid/ethyl acrylate copolymer such as that sold as Tilamar Fix A-1000 by DSM; copolymers derived from crotonic acid, such as vinyl acetate/vinyl tertbutylbenzoate/crotonic acid terpolymers and the crotonic acid/vinyl acetate/vinyl neododecanoate terpolymers such as that sold as Resin 282930 by Akzo Nobel. Preferred hairstyling polymers derived from sulfonic acid include: sodium polystyrene sulfonate sold as Flexan 130 by Ashland; sulfopolyester (also known as Polyester-5) such as that sold as Eastman AQ 48 by Eastman; sulfopolyester (also known as Polyester-5) such as that sold as Eastman AQ S38 by Eastman; sulfopolyester (also known as Polyester-5) such as that sold as Eastman AQ 55 by Eastman. In at least one embodiment, the anionic hairstyling polymers are preferably selected from: copolymers derived from acrylic acid such as the acrylic acid/ethylacrylate/N-tert-butylacrylamide terpolymers (such as that sold as Ultrahold 8 by BASF); Octylacrylamide/Acrylates/Butylaminoethyl/Methacrylate Copolymer such as that sold as Amphomer; methacrylic acid/ester acrylate/ester methacrylate such as that sold as Balance CR by Akzo Nobel; Octylacrylamide/Acrylates/ Butylaminoethyl Methacrylate Copolymer such as that sold as Balance 47 by Akzo nobel; methacrylic acid/hydroxyethylmethacrylate/various acrylate esters such as that known as Acudyne 1000 sold by Dow Chemical; acrylates/hydroxyethylmethacrylate such as that sold as Acudyne 180 by Dow Chemical; methacrylic acid/hydroxyethylmethacrylate/various acrylate esters such as that sold as Acudyne DHR by Dow Chemical; n-butyl methacrylate/methacrylic acid/ethyl acrylate copolymer such as that sold as Tilamar Fix A-1000 by DSM; copolymers derived from crotonic acid, such as vinyl acetate/vinyl tertbutylbenzoate/crotonic acid terpolymers and the crotonic acid/vinyl acetate/vinyl neododecanoate terpolymers such as that sold as Resin 282930 by Akzo Nobel. Preferred hairstyling polymers derived from styrene sulfonic acid include: sodium polystyrene sulfonate sold as Flexan 130 by Ashland; sulfopolyester (also known as Polyester-5) such as that sold as Eastman AQ 48 by Eastman; sulfopolyester (also known as Polyester-5) such as that sold as Eastman AQ S38 by Eastman; sulfopolyester (also known as Polyester-5) such as that sold as Eastman AQ 55 by Eastman.

In an embodiment, the hairstyling polymer is an anionic hairstyling polymer, and wherein the anionic hairstyling polymer is selected from: copolymers derived from acrylic acid such as the acrylic acid/ethylacrylate/N-tert-butylacrylamide terpolymers; Octylacrylamide/Acrylates/Butylaminoethyl/Methacrylate Copolymers; methacrylic acid/ester acrylate/ester methacrylates; Octylacrylamide/Acrylates/ Butylaminoethyl Methacrylate Copolymer; methacrylic acid/hydroxyethylmethacrylate/various acrylate esters; acrylates/hydroxyethylmethacrylate; methacrylic acid/hydroxyethylmethacrylate/various acrylate esters; n-butyl methacrylate/methacrylic acid/ethyl acrylate copolymers; copolymers derived from crotonic acid, such as vinyl acetate/vinyl tertbutylbenzoate/crotonic acid terpolymers; and the crotonic acid/vinyl acetate/vinyl neododecanoate terpolymers; and mixtures thereof.

In an embodiment, the hairstyling polymer is a polyurethane dispersed in water. Such polyurethanes include those such as adipic acid, 1-6 hexandiol, neopentyl glycol, isophorone diisocyanate, isophorone diamine, N-(2-aminoethyl)-3-aminoethanesulphonic acid, sodium salt (also known as Polyurethane-48) such as that sold as Baycusan C1008 by Bayer; and such as isophorone diisocyanate, dimethylol propionic acid, 4,4-isopropylidenediphenol/propylene oxide/ethylene oxide (also known as Polyurethene-14) such as that sold as a mixture under the name of DynamX H20 by AkzoNobel.

In an embodiment, the hairstyling polymer is a nonionic hairstyling polymer or a mixture of nonionic hairstyling polymers. Suitable synthetic non-ionic hairstyling polymers include: homopolymers and copolymers comprising: (a) at least one of the following main monomers: vinylpyrrolidone; vinyl esters grafted onto a polyalkylene glycol such as polyethylene glycol; acrylate esters grafted onto a polyalkylene glycol such as polyethylene glycol or acrylamide and (b) one or more other monomers such as vinyl esters (e.g. vinyl acetate or vinyl propionate, vinyl tert-butyl-benzoate); alkylacrylamine (e.g. tert-butylamino-ethyl methacrylate, dimethyl aminoethyl methacrylate); vinylcaprolactam; hydroxyalkylated acrylamide; amino alkylated acrylamide (e.g. dimethyl amino propyl methacrylamide); vinyl ether; alkyl maleimide, hydroxyalkyl maleimide (e.g. Ethyl/Ethanol Maleimide).

In an embodiment, the non-ionic hairstyling polymer is preferably selected from vinylpyrrolidone/vinyl acetate copolymers (such as that sold as LUVISKOL VA 64 by BASF and such as vinylpyrrolidone homopolymer such as that sold as PVPK30 by Ashland).

In an embodiment, the non-ionic hairstyling polymer is a water-soluble natural polymer being a cellulose derivative, such as hydroxyalkylcelluloses (e.g. hydroxymethyl-, hydroxyethyl- or hydroxypropylcelluloses) and starches.

In an embodiment, the hairstyling polymer is an amphoteric hairstyling polymer or a mixture of amphoteric hairstyling polymers. Suitable synthetic amphoteric hairstyling polymers include those comprising: an acid and a base like monomer; a carboxybetaine or sulfobetaine zwitterionic monomer; and an alkylamine oxide acrylate monomer. In at least one embodiment, the amphoteric comprising: (a) at least one monomer containing a basic nitrogen atom such as a quaternized dialkylaminoalkyl acrylamide (e.g. Quaternized dimethyl amino propyl methacrylamide) or a quaternized dialkylaminoalkyl acrylate (e.g. quaternized dimethyl aminoethyl methacrylate) and (b) at least one acid monomer comprising one or more carboxylic or sulfonic groups such as acrylic acid, or methacrylic acid or crotonic acid or their salts, or C4-C8 monounsaturated polycarboxylic acids or anhydrides (e.g. maleic, furamic, itaconic acids and their anhydrides) and (c) one or more monomers selected from acrylamides, methacrylamides which may or may not be substituted on the nitrogen by lower alkyl groups (C1-C4) (e.g. N-tertbutylacrylamide); vinyllactams such as vinylpyrrolidone or vinylcapro lactam; esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. In an embodiment, the amphoteric hairstyling polymer comprises at least one carboxybetaine or sulfobetaine zwitterionic monomer such as carboxybetaine methacrylate and sulfobetaine methacrylate. In at least one embodiment, the amphoteric hairstyling polymer comprises: (a) at least one carboxybetaine or sulfobetaine zwitterionic monomer such as carboxybetaine methacrylate and sulfobetaine methacrylate; and (b) a monomer selected from the group consisting of: acrylamides, methacrylamides which may or may not be substituted on the nitrogen by lower alkyl groups (C1-C4) (e.g. N-tertbutylacrylamide); vinyllactams such as vinylpyrrolidone or vinylcapro lactam; esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. In at least one embodiment, the amphoteric hairstyling polymer comprises at least an alkylamine oxide acrylate. In at least one embodiment, the amphoteric hairstyling polymer comprises: (a) an ethylamine oxide methacrylate; and (b) a monomer selected from the group consisting of: acrylamides, methacrylamides which may or may not be substituted on the nitrogen by lower alkyl groups (C1-C4) (e.g. N-tertbutylacrylamide); vinyllactams such as vinylpyrrolidone or vinylcapro lactam; esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. An example of such an amphoteric hairstyling polymer is acrylates/ethylamine oxide methacrylate sold as Diaformer Z 731 N by Clariant.

In an embodiment, the hairstyling polymer is selected from the group consisting of: acrylates copolymers of two or more monomers of (meth)acrylic acid or one of their simple esters; octylacrylamide/acrylate/butylaminoethyl methacrylate copolymers; acrylates/hydroxyesters acrylates copolymers of butyl acrylate, methyl methacrylate, methacrylic acid, ethyl acrylate and hydroxyethyl methacrylate; polyurethane-14/AMP-acrylates copolymer blend; and mixtures thereof.

In an embodiment, the hairstyling formulation may be substantially free of water-insoluble polymers, in particular, water-insoluble hairstyling polymers. Polymers that are not miscible in water should be avoided for the present invention. Polymers of high molecular weight (>200,000 g/mol) should be or only used at very low levels such that the hairstyling formulation does not exceed the viscosity requirements. In an embodiment, the polymer may be water soluble. In at least one embodiment, the hairstyling formulation is substantially free of a polymer having a molecular weight of greater than 200,000 g/mol. In at least one embodiment, the hairstyling formulation is substantially free of a polymer comprising at least two long hydrophobic (e.g. linear fatty chains of 10 carbons or more) grafts. Such polymers with such grafts can lead to associative interactions in the hairstyling formulation which can drive viscosity up without contributing to the strength of the film delivered to the hair.

Optional Ingredients

In an embodiment, the hairstyling formulation may comprises a panthenol compound and/or a silicone compound. In an embodiment, the panthenol compound is selected from the group consisting of: panthenol, a pantothenic acid derivative, and mixtures thereof. In at least one embodiment, the panthenol compound is selected from the group consisting of: D-panthenol ([R]-2,4-dihydroxy-N-[3-15-(hydroxypropyl)]-3,3-dimethylbutamide), D/L-panthenol, pantothenic acids and their salts, panthenyl triacetate, royal jelly, panthetine, pantotheine, panthenyl ethyl ether, pangamic acid, pantoyl lactose, Vitamin B complex, and mixtures thereof. The panthenol compound may be useful in view of providing excellent hair look and feel benefits. The hairstyling formulation may comprise from about 0.1% to about 0.6%, or from about 0.1% to about 0.3%, of a panthenol compound, by total weight of the hairstyling formulation and the propellant. In at least one embodiment, the hairstyling formulation comprises a silicone compound. The silicone may be useful because it gives a smoother feel and also shine to the hair. In at least one embodiment, the silicone compound is a dimethicone compound. In at least one embodiment, the silicone compound is a PEG dimethicone, for example PEG-12 dimethicone.

The hairstyling formulation may further comprise a surfactant. The hairstyling formulation may comprise 1% or less surfactant, or 0.6% or less, or 0.4% or less, or 0.3% or less, by total weight of the hairstyling formulation and propellant. In at least one embodiment, the surfactant is selected from the group consisting of: cationic surfactants, non-ionic surfactants, anionic surfactants, and mixtures thereof. Cationic surfactants may be selected from the group consisting of cetrimonium chloride (e.g. Quartamin 60L-G from Kao; DEHYQUART A-CA/DETEX; ARQUAD 16-25 LO); cocamidopropyl hydroxysultaine (e.g. REWOTERIC AM CAS); cocamidopropyl betaine (e.g. TEGO BETAIN F 50); betaine; and mixtures thereof. Non-ionic surfactants may be selected from the group consisting of: castor oil PEG-40 H (e.g. NEODOL10 91-8); laureth-4 (e.g. DEHYDOL LS 4 DEO N); laureth-9; decyl glucoside (e.g. Plantacare 2000); polysorbate 20 (e.g. TWEEN 20 PHARMA from UNIQEMA); PEG-25 hydrogenated castor oil (e.g. SIMULSOL 1292 DF from SEPPIC); PEG-40 hydrogenated castor oil (e.g. CREMOPHOR CO 410 from BASF); PPG-1-PEG-9-laurylglycolether (e.g. Eumulgin L); siloxane polyalkyleneoxide copolymer (Silwet® L7604 from Momentive); and polydimethylsiloxane methylethoxylate (Silwet® L7600 from Momentive); and mixtures thereof. A suitable anionic surfactant is dioctyl sodium sulfosuccinate (DOSS or 1,4-dioctoxy-1,4-dioxobutane-2-sulfonic acid), an example of which is Aerosol OT-70 PG from Cytec. In at least one embodiment, the surfactant is selected from the group consisting of: castor oil PEG-40 H; cetrimonium chloride; laureth-4; laureth-9; decyl glucoside; cocamidopropyl hydroxysultaine; polysorbate 20; siloxane polyalkyleneoxide copolymer; dioctyl sodium sulfosuccinate; and mixtures thereof In an embodiment, the hairstyling formulation may comprise a neutraliser. Suitable neutralisers include potassium hydroxide, sodium hydroxide, triisopropanolamine (TIPA), 2-aminobutanol, 2-aminomethyl propanol (AMP), aminoethylpropandiol, dimethyl stearamine (Armeen 18 D), sodium silicate, tetrahydroxypropyl ethylenediamine (Neutrol® TE), ammonia (NH3), triethanolamine, trimethylamine (Tris AminoUltra), aminomethylpropandiol (AMPD). In at least one embodiment, the neutralising agent is 2-aminobutanol, ammonia, or 2-aminomethyl propanol.

In an embodiment, the hairstyling formulation may comprise one or more perfume microcapsules.

The hairstyling formulation may comprise at least one preservative. The preservative may be present in an amount of less than about 1.5%, or 0% to 1%, or 0.01% to 1%, by total weight of the hairstyling formulation and propellant. Suitable preservatives include: phenoxyethanol (e.g. Euxyl® PE 9010), benzyl alcohol, propylene glycol, PHMB (Poly-aminopropyl biguanide), Optiphen (Phenoxyethanol+caprylyl glycol) from ISP, Symtriol (1,2-octanediol and 1,2 hexanediol, methylbenzyl alcohol) from Symrise, octylsalicylate, 1,3-bis(hydroxymethyl)-5,5-dimethylimidazolidine-2,4-dione (DMDM hydantoin; Nipaguard® DMDMH by Clariant), EDTA (Rexat), butylene glycol (Dekaben LMB), and parben types e.g. methylparaben (e.g. PHB methyl ester from Schütz & Co., or SLI Chemicals, or Nipagin® M), propylparaben (PHB—propylester from Solvadis Specialties).

The hairstyling formulation may further comprise at least one perfume or fragrance. The hairstyling formulation may comprise a maximum of about 0.5% perfume or fragrance, or from about 0% to about 0.4%, or from about 0.03% to about 0.3%, by total weight of the hairstyling formulation and propellant.

In at least one embodiment, the hairstyling formulation may comprise a corrosion inhibitor. In at least one embodiment, the corrosion inhibitor is EDTA.

The hairstyling formulation may further comprise vitamins and amino acids such as: water-soluble vitamins such as vitamin B1, B2, B6, B12, C, pantothenic acid, pantothenyl ethyl ether, panthenol, biotin, and their derivatives, water soluble amino acids such as asparagine, alanine, indole, glutamic acid and their salts, water insoluble vitamins such as vitamin A, D, E, and their salts and/or derivatives, water insoluble amino acids such as tyrosine, tryptamine, viscosity modifiers, dyes, non-volatile solvents or diluents (water soluble and insoluble), pearlescent aids, foam boosters, additional surfactants or non-ionic cosurfactants, pediculocides, pH adjusting agents, perfumes, preservatives, chelants, proteins, skin active agents, sunscreens, UV absorbers, vitamins, niacinamide, caffeine and minoxidil. The hairstyling formulation may comprise from about 0.01% to about 5% vitamins and/or amino acids, by total weight of the hairstyling formulation and propellant. The hairstyling formulation may further comprise pigment materials such as inorganic pigments, nitroso-, monoazo-, disazocompounds, carotenoid, triphenyl methane, triaryl methane, chemicals of the quinoline, oxazine, azine, or anthraquinone type, as well as compounds which are indigoid, thionindigoid, quinacridone, phthalocianine, botanical, natural colors, and water-soluble components. The hairstyling formulation may comprise from about 0.0001% to about 5% pigment materials, by total weight of the hairstyling formulation and propellant. The hairstyling formulation may also contain antimicrobial agents which are useful as cosmetic biocides. The hairstyling formulation may comprise from about 0.01% to about 5% antimicrobial agents, by total weight of the hairstyling formulation and propellant.

Propellant

The aerosol hairspray product may comprise from about 30% to about 60%, alternatively from about 35% to about 55%, alternatively from about 40% to about 50% of the dimethyl ether propellant, by total weight of the hairstyling formulation and the dimethyl ether propellant. Dimethyl ether may be useful in the invention in view of it forming a homoegeous solution with the hairstyling formulation.

In an embodiment, the dimethyl ether propellant and the hairstyling formulation freely communicate with one another inside the reservoir. In an embodiment, the liquefied gas propellant and hairstyling formulation are not stored in separate compartments.

The aerosol hairspray product comprises a container (100) comprising a container wall (110) which encloses a reservoir (120). The pressure inside the reservoir (120) may be measured with a pressure gauge (GCAS #60001439). In an embodiment, the pressure inside the container is from about 1 bar to about 7 bar, or from about 1.5 bar to about 5 bar, measured at 20° C.

Spraying Device

The aerosol hairspray product comprises a spraying device (200) attached to the container (100) for dispensing the hairstyling formulation (180) from the reservoir (120) of the container (100); wherein the spraying device (200) is fluidly connected to the reservoir (120); wherein the spraying device (200) comprises a spray actuator (150) and a valve (130); wherein the valve (130) comprises a valve housing (140); wherein the valve housing (140) comprises a vapor tap (160); wherein the vapor tap (160) comprises a vapor tap area; wherein a dip tube (170) is fluidly connected to the valve (130); wherein the dip tube (170) comprises a dip tube orifice (175); wherein the dip tube orifice (175) comprises a dip tube orifice area; and wherein the ratio of the vapor tap area to the dip tube orifice area is from about 0.005 to about 0.15, alternatively from about 0.006 to about 0.125, alternatively from about 0.007 to about 0.1, alternatively from about 0.008 to about 0.09, alternatively from about 0.009 to about 0.08, and alternatively from about 0.0095 to about 0.07. In an embodiment, the ratio of the vapor tap area to the dip tube orifice area is about 0.063 or about 0.011.

The ratio of the vapor tap area to the dip tube orifice area may be important to prevent clogging and to maintain an acceptable spray droplet size.

In an embodiment, the valve housing (140) does not comprise two or more vapor taps (160).

Method

In an embodiment, a hairstyling method is provided comprising (a) providing an aerosol hairspray product comprising (1) a container (100) comprising a container wall (110) which encloses a reservoir (120), wherein the reservoir (120) comprises from about 40% to about 70% of a hairstyling formulation and from about 30% to about 60% of a dimethyl ether propellant, by total weight of the hairstyling formulation and the dimethyl ether propellant; (2) wherein the hairstyling formulation comprises (i) from about 30% to about 60% water, by total weight of the hairstyling formulation and the dimethyl ether propellant; (ii) from about 5% to about 15% of one or more hairstyling polymers by total weight of the hairstyling formulation and the dimethyl ether propellant, wherein the hairstyling polymer is water-soluble and has a molecular weight of less than 200,000 g/mol; (iii) from about 0.05% to about 2% alcohol, by total weight of the hairstyling formulation and the dimethyl ether propellant; and (iv) is substantially free of ethanol; wherein the hairstyling formulation has a viscosity of from about 2.5 cSt to about 5.5 cSt; (3) a spraying device (200) attached to the container (100) for dispensing the hairstyling formulation from the reservoir (120) of the container (100); wherein the spraying device (200) is fluidly connected to the reservoir (120); wherein the spraying device (200) comprises a spray actuator (150) and a valve (130); wherein the valve (130) comprises a valve housing (140); wherein the valve housing (140) comprises a vapor tap (160); wherein the vapor tap (160) comprises a vapor tap area; wherein a dip tube (170) is fluidly connected to the valve (130); wherein the dip tube (170) comprises a dip tube orifice (175); wherein the dip tube orifice (175) comprises a dip tube orifice area; and wherein the ratio of the vapor tap area to the dip tube orifice area is from about 0.005 to about 0.15; and (c) causing the aerosol hairspray product to spray at a delivery rate, wherein the delivery rate is from about 0.28 g/sec to about 0.45 g/sec; and wherein an ejected composition is sprayed, wherein the ejected composition comprises particles having a Dv50 droplet size of from about 40 micron to about 100 micron and a Dv90 droplet size of from about 160 micron to about 300 micron.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

TABLE 1

| | A | B | C | D | E | F | G | H |
|---|---|---|---|---|---|---|---|---|
| | | | Concentrate ingredient (% active) | | | | | |
| Acrylates Copolymer [1] | 12.3% | 4.8% | 8.4% | — | — | — | — | — |
| Polyurethane-14/AMP-acrylates polymer blend [2] | — | 4.8% | 2.1% | 19% | 11% | — | — | — |
| Octylacrylamide/Acrylates/Butylaminoethyl/Methacrylate Copolymer [4] | — | — | 1.2% | — | 2.0% | — | — | — |
| Vinylpyrrolidone/Vinylacetate Copolymer [5] | — | — | — | — | — | 10.8% | — | 9.58% |
| Methacrylic acid/hydroxyethylmethacrylate/various acrylate esters [3] | — | 2.40% | — | — | — | — | — | — |
| Polyquaternium-16 [6] | — | — | — | — | — | — | 6.7% | — |

TABLE 1-continued

|  | A | B | C | D | E | F | G | H |
|---|---|---|---|---|---|---|---|---|
|  | Concentrate ingredient (% active) | | | | | | | |
| Chitosan [7] | — | — | — | — | — | — | 1.25% | — |
| Hydroxyethylcellulose dimethyldiallyammonium chloride[PQ4] [8] | — | — | — | — | — | — | — | 0.83% |
| 2-aminomethyl propanol (AMP) | 1.73% | 1.36% | 1.42% | — | 0.39% | — | — | — |
| Formic Acid | — | — | — | — | — | — | 0.40% | — |
| Fragrance | 0.03% | 0.10% | 0.10% | 0.10% | 0.10% | 0.18% | 0.15% | 0.2% |
| Dehyquart A-CA/Detex (cationic surfactant) | 0.4% | 0.4% | 0.4% | — | 0.40% | 0.4% | 0.4% | 0.4% |
| Dehydol LS 4 Deo N (Non-ionic surfactant) | 0.1% | 0.1% | — | 0.10% | — | — | — | 0.10% |
| PEG-12 dimethicone | 0.10% | — | — | — | — | — | — | — |
| Disodium EDTA | 0.13% | 0.13% | 0.13% | 0.13% | 0.13% | 0.13% | 0.13% | 0.13% |
| Phenoxyethanol | 0.50% | 0.50% | 0.50% | 0.50% | 0.50% | 0.50% | 0.50% | 0.50% |
| Methylparaben | 0.10% | 0.10% | 0.10% | 0.10% | 0.10% | 0.10% | 0.10% | 0.10% |
| Water | QSP | QSP | QSP | QSP | QSP | QSP | QSP | QSP |
| Propellant % | 40 | 40 | 50 | 45 | 50 | 50 | 45 | 40 |
| Concentrate % | 60 | 60 | 50 | 55 | 55 | 50 | 55 | 60 |
| Vapor tap orifice area, in$^2$ (mm$^2$) | 0.00013 (0.084) | 0.000079 (0.051) | 0.00013 (0.084) | 0.000079 (0.051) | 0.00018 (0.116) | 0.00026 (0.168) | 0.00013 (0.084) | 0.000079 (0.051) |
| Dip tube orifice area in$^2$ (mm$^2$) | 0.0117 (7.55) | 0.0117 (7.55) | 0.00126 (0.813) | 0.00126 (0.813) | 0.00126 (0.813) | 0.0117 (7.55) | 0.0117 (7.55) | 0.0117 (7.55) |
| Ratio of VT area/DT area | 0.011 | 0.006 | 0.103 | 0.063 | 0.143 | 0.022 | 0.011 | 0.006 |

KEY:
[1] = Balance CR;
[2] = DynamX H20;
[3] = Acudyne 1000;
[4] = Amphomer;
[5] = Luviskol VA64;
[6] = Luviquat FC550;
[7] = Hydagen ® HCMF;
[8] = Celquat L-200.

The examples in Table 1 may be made using a conventional method of making hairstyling formulations and products.

DATA

TABLE 2

| Key valve part measurement ranges | | | |
|---|---|---|---|
|  | Valve 1 | Valve 2 | Valve 3 |
| Vapor tap area, in$^2$ (mm$^2$) VT | 0.00026 (0.168) | 0.000079 (0.051) | 0.00013 (0.084) |
| Dip tube orifice* inner diameter area in$^2$ (mm$^2$) DT | 0.00126 (0.813) | 0.00126 (0.813) | 0.0117 (7.55) |
| Ratio of VT area/DT orifice area | 0.207 | 0.063 | 0.011 |

Figure 3:
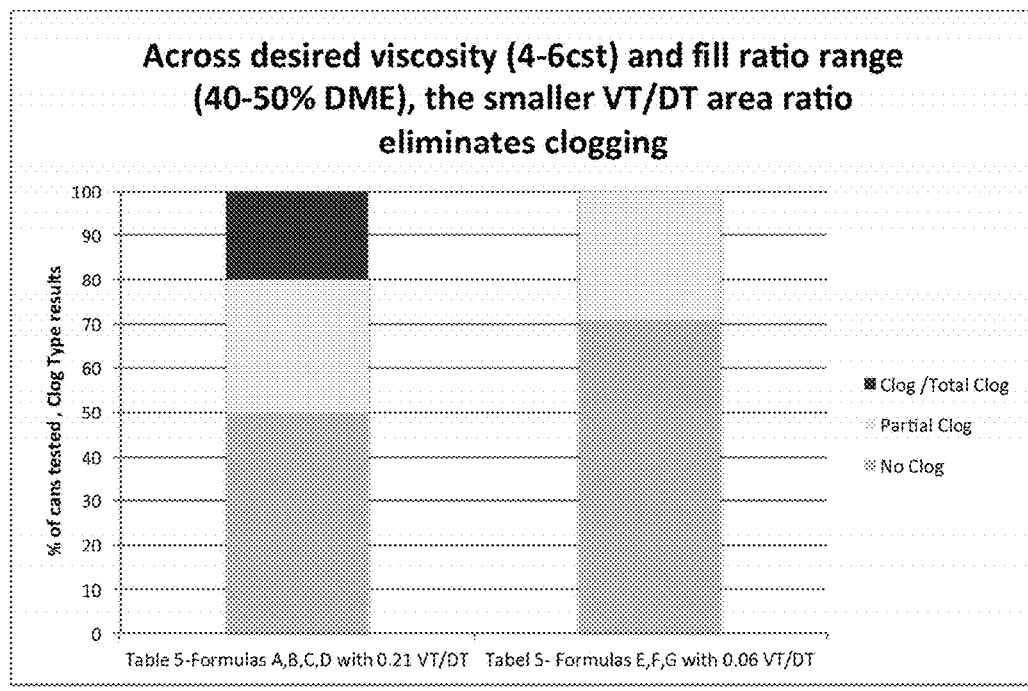
FIG. 3 is a bar graph showing that the vapor tap area to dip tube orifice area ratio (VT/DT) of the aerosol hairspray product described herein results in no clogs vs. the larger VT/DT area ratio.

The vapor tap area to dip tube orifice area ratio (VT/DT) described herein results in no clogs vs. the larger VT/DT (FIG. 3). A type 3 or 4 clog is one where the spray does not come out of the actuator when it is depressed. This is surprising because one would expect a large vapor tap that delivers a large amount of vaporous propellant to the flow path to reduce clog potential in comparison to a smaller vapor tap. However, data shows that introducing less vaporous propellant and more liquid propellant into the flow path per spray, helps clear any residual hairspray material more effectively. The theory is that more liquid propellant in flow path will vaporize to hundreds of times it's volume at exiting and clear out any potential clog material. When the hairspray actuator button is depressed, the dip tube introduces the liquid propellant into the flow path and the vapor tap introduces the vaporous propellant into the same flow path. It is the balancing of this ratio that eliminates clogging, improves life of can performance Keeping the VT/DT area as described herein eliminates the clogging that occurs at higher ratios.

Aerosol Spray Clog Measurement Method

The purpose of this routine method is to determine the level of incidence and severity of clogging of an aerosol. A minimum of 10 replicate cans is conditioned at 21 degrees Celsius for a minimum of one hour. The testing is run at room temperature (20 to 24 degrees Celcius). Each of the replicate cans is sprayed for 5 to 10 seconds. After the spray, the cans are not disturbed for 24 hours. After 24 hours, the clogging assessment is determined by firmly pressing the actuator and assigning a classification of clog severity according to the following table:

TABLE 3

| Clog type result categorization and description | | |
|---|---|---|
| Type/Category of Clog | Description of Clog | Description of Observation |
| Category 1 | No Clog | The can gives a good quality spray without any spitting/streaming likely to be noticed by a consumer |

TABLE 3-continued

Clog type result categorization and description

| Type/Category of Clog | Description of Clog | Description of Observation |
|---|---|---|
| Category 2 | Partial Clog | The can exhibits an abnormal or deformed spray when first actuated. Product flow may be reduced. This may be noticed by a consumer. |
| Category 3 | Clog | The can does not spray at all when first actuated, but clears after actuating ten times or rinsing with warm water (actions a consumer is likely to take). This is judged to have considerable impact on the consumer. |
| Category 4 | Total Clog | The can does not spray at when first actuated, and CANNOT be cleared by actuating ten times or rinsing actuator in warm water. The can is inoperable. The sample is removed from the test and noted as a failure. This category of clog has the maximum impact on a consumer. |

If a can does not produce any spray initially, a) actuate can 10 times b) rinse actuator with warm water. If neither of these actions restores the spray then this can is deemed to be a Total Clog and is discarded from the test. Repeat the test every 24 hours on the same set of replicate cans over a period of at least 2 weeks.

Figure 4:
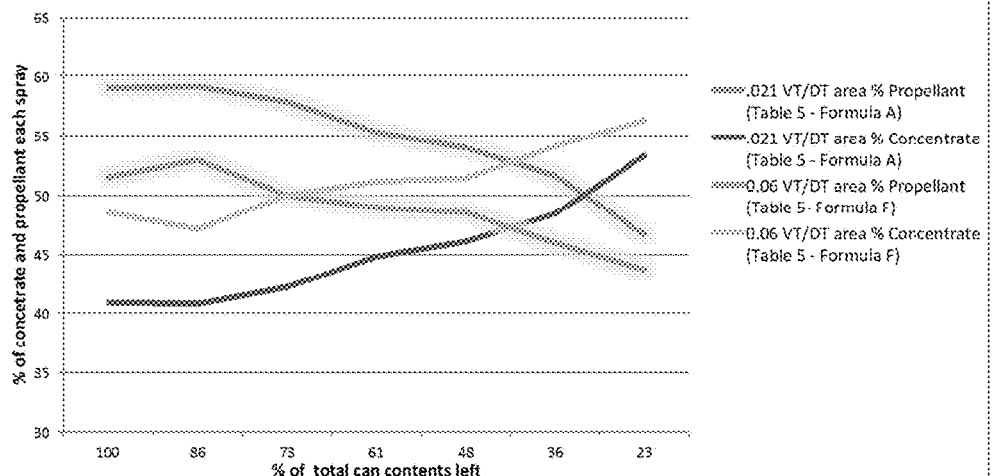
FIG. 4 is a line graph showing the amount of concentrate delivered at different VT/DT area ratios.

The VT area/DT orifice area ratios described herein may deliver a more consistent and target amount of concentrate and propellant for each spray through the life of the can. FIG. 4 below, shows the VT/DT area ratio delivers a more consistent and target amount of concentrate and propellant for each spray through the life of the can. For the same fill ratio, of the same formula, the larger VT/DT area ratio is delivering a below target concentrate level for the majority of the can life in addition to the high clogging incidences. The concentrate liquid of an aerosol product is designed around how much will be filled in the can and dispensed. For example, if one wants to deliver 5% polymer from a hairspray and the final aerosol will be filled with 50% liquid concentrate and 50% propellant, the liquid concentrate before filling would be prepared at a 10% polymer level, to deliver the target 5%. Therefore, ensuring you are delivering the target fill ratio is vital to intended performance. The ratio of liquid concentrate to propellant being dispensed from the finished product can was measured using the "Concentrate Spray Rate Measurement Method."

Concentrate Spray Rate Measurement Method

This test method may be used to determine the liquid concentrate spray rate of aerosol products, where propellant is permanently mixed with the concentrate and the valve utilizes a vapor tap. During the test the product is dispensed into a plastic bag. The propellant is then evaporated leaving only the concentrate, which is measured by weighing. Procedure:

Place product in a water bath set up at 21+/−1 degree Celsius for 5 minutes

Remove product from water bath and dry

Record initial weight of product (S1), Record initial weight of plastic bag (C1)

Open plastic bag fully to create a large pocket for product to spray into and then close plastic bag leaving only a 2 inch hole open (this limits concentrate exiting bag after spraying into it)

Shake product vigorously by hand for 10 seconds to ensure uniform distribution of the concentrate and propellant in the can Spray for 5 seconds into a small opening in plastic bag (keep opening as close to the can as possible to make sure all product is sprayed into the bag, hold the bag closed.

Hold the plastic bad with opening facing up for 15 seconds to allow the maximum amount of concentrate to settle onto bag lining Open plastic bag gently to let the propellant evaporate from the bag Fold bag and record weight (C2), Record weight of can after spray (S2)

Calculations:

$(S2-S1)/5$ sec=$S$ (g/sec)    Total spray rate (S):

$(C2-C1)/5$ sec=$C$ (g/sec)    Concentrate spray rate (C):

$C/S*$% propellant filled in the can    % Valve balance:

Now referring to FIG. 4, FIG. 4 shows that for the same concentrate at the same fill ratio (50/50), the larger VT/DT area ratio delivers an inconsistent and off-tar-get amount of propellant and concentrate from the beginning to the end of the can.

TABLE 4

Example - delivering 5% Target polymer at two different fill ratios and concentrate viscosities

| | % polymer in finished product - 50C/50P fill/delivery ratio | % polymer in finished product - 60C/40P fill/delivery ratio | Concentrate viscosity |
|---|---|---|---|
| 10% Polymer in Concentrate | 5% target | 6% | 5 cst |
| 8.35% Polymer in Concentrate | 3.34% | 5% target | 4 cst |

Figure 5:
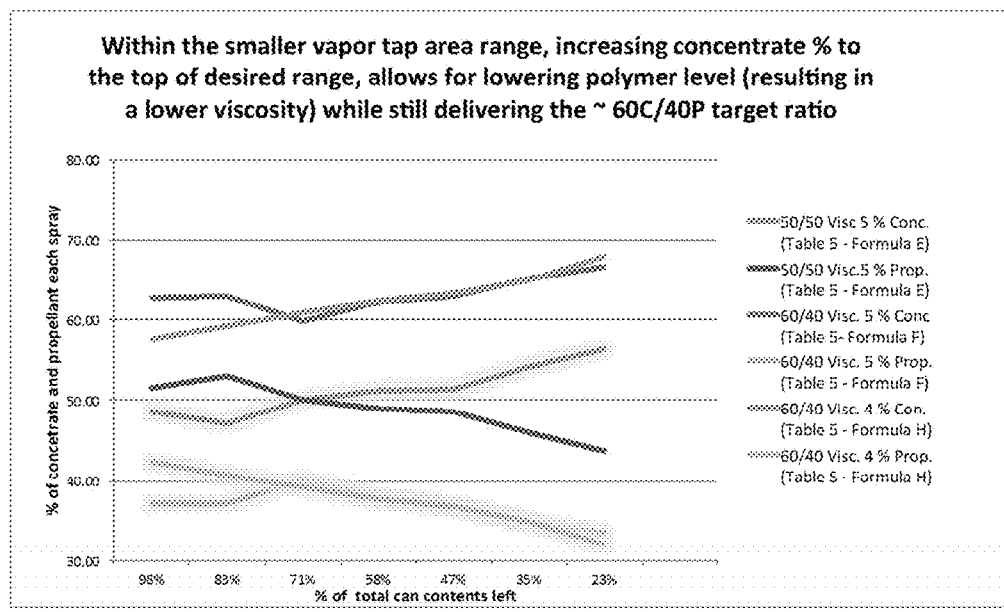
FIG. 5 is a line graph showing the results of different concentrate fill ratios over the life of the aerosol hairspray product.

Now referring to FIG. 5, FIG. 5 shows that within the smaller vapor tap area range, increasing concentrate % to the top of the desired rane allows for lowering the polymer level (resulting in a lower viscosity) while still delivering ~60C/40P target ratio.

Now referring to FIG. 6, FIG. 6 shows that a 60C/40P ratio at a lower concentrate viscosity within the desired VT/DT area range results in target delivery, no clogging, and the smallest overall Dv50 and Dv90 droplet size through the life of the can.

This option also eliminates a noticeable sputtering when the button is released at the end of the product spray. This reduction in sputtering is a result of less liquid propellant residing in the flow path, and a thinner concentrate at dispensing which reduces the forcefulness of propellant release and the thickness of concentrate at dispensing. These two features also further reduce deformed spray incidences.

Now referring to FIG. 7, FIG. 7 shows less cut-off and sputter/spray deformities enabled by the VT/DT area ratio range with a target delivery ratio and concentrate viscosity.

Table 5 below depicts alcohol-free hairspray formulations at the fill ratios and with the VT/DT ratios tested to provide the experimental data.

TABLE 5

Concentrate formula, fill ratio and valve + dip tube area ratio used for data

| | A (control) | B (control) | C (control) | D (control) | E | F | G | H |
|---|---|---|---|---|---|---|---|---|
| | | | Concentrate ingredient (% active) | | | | | |
| Acrylates Copolymer [1] | 4.8% | 4.8% | 4.8% | 9.6% | 4.8% | 4.8% | 4.8% | 4.1% |
| Polyurethane-14/AMP-acrylates polymer blend [2] | 4.8% | 4.8% | 4.8% | 0.0% | 4.8% | 4.8% | 4.8% | 4.1% |
| Methacrylic acid/ hydroxyethylmethacrylate/ various acrylate esters[3] | 2.4% | 2.4% | 2.4% | 4.1% | 2.4% | 2.4% | 2.4% | 2.1% |
| 2-aminomethyl propanol | 0.57% | 0.57% | 0.57% | 1.08% | 0.57% | 0.57% | 0.57% | 0.49% |
| Potassium Hydroxide | 0.75% | 0.75% | 0.75% | 1.43% | 0.75% | 0.75% | 0.75% | 0.64% |
| Fragrance | 0.3% | 0.3% | 0.3% | 0.3% | 0.3% | 0.3% | 0.3% | 0.3% |
| Dehyquart A-CA/Detex | 0.4% | 0.4% | 0.4% | 0.4% | 0.4% | 0.4% | 0.4% | 0.40% |
| Dehydol LS 4 Deo N | 0.1% | 0.1% | 0.1% | 0.1% | 0.1% | 0.1% | 0.1% | 0.1% |
| PEG-12 dimethicone | 0.25% | 0.25% | 0.25% | — | 0.25% | 0.25% | 0.25% | — |
| Disodium EDTA | 0.13% | 0.13% | 0.13% | 0.13% | 0.13% | 0.13% | 0.13% | 0.13% |
| Preservative system | 0.70% | 0.70% | 0.70% | 0.70% | 0.70% | 0.70% | 0.70% | 0.70% |
| Water | QSP | QSP | QSP | QSP | QSP | QSP | QSP | QSP |
| Concentrate % | 50 | 60 | 55 | 55 | 50 | 60 | 55 | 60 |
| Propellant % | 50 | 40 | 45 | 45 | 50 | 40 | 45 | 40 |
| Vapor tap orifice area, in$^2$ (mm$^2$) | 0.00026 (0.168) | 0.00026 (0.168) | 0.00026 (0.168) | 0.00026 (0.168) | 0.000079 (0.051) | 0.000079 (0.051) | 0.000079 (0.051) | 0.000079 (0.051) |
| Dip tube orifice area in$^2$ (mm$^2$) | 0.00126 (0.813) | 0.00126 (0.813) | 0.00126 (0.813) | 0.00126 (0.813) | 0.00126 (0.813) | 0.00126 (0.813) | 0.00126 (0.813) | 0.00126 (0.813) |
| Ratio VT area/DT area | 0.21 | 0.21 | 0.21 | 0.21 | 0.06 | 0.06 | 0.06 | 0.06 |

KEY:
[1] = Balance CR;
[2] = DynamX H20;
[3] = Acudyne 1000

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. An aerosol hairspray product comprising:
    i. a container (100) comprising a container wall (110) which encloses a reservoir (120), wherein the reservoir (120) comprises from about 40% to about 70% of a hairstyling formulation and from about 30% to about 60% of a dimethyl ether propellant, by total weight of the hairstyling formulation and the dimethyl ether propellant;
    ii. wherein the hairstyling formulation comprises:
        (a) from about 30% to about 60% water, by total weight of the hairstyling formulation and the dimethyl ether propellant;
        (b) from about 5% to about 15% of one or more hairstyling polymers by total weight of the hairstyling formulation and the dimethyl ether propellant, wherein the hairstyling polymer is water-soluble and has a molecular weight of less than 200,000 g/mol;
        (c) is substantially free of ethanol;
    wherein the hairstyling formulation has a viscosity of from about 2.5 cSt to about 5.5 cSt;
    iii. a spraying device (200) attached to the container (100) for dispensing the hairstyling formulation (180) from the reservoir (120) of the container (100);
        wherein the spraying device (200) is fluidly connected to the reservoir (120);
        wherein the spraying device (200) comprises a spray actuator (150) and a valve (130);
        wherein the valve (130) comprises a valve housing (140);
        wherein the valve housing (140) comprises a vapor tap (160);
        wherein the vapor tap (160) comprises a vapor tap area;

wherein a dip tube (170) is fluidly connected to the valve (130);
wherein the dip tube (170) comprises a dip tube orifice (175);
wherein the dip tube orifice (175) comprises a dip tube orifice area;
wherein the ratio of the vapor tap area to the dip tube orifice area is from about 0.063 to about 0.15;
wherein the vapor tap area to dip tube orifice area ratio results in no clogs according to the Aerosol Spray Clog Measurement Method.

2. The aerosol hairspray product of claim 1, wherein the one or more hairstyling polymers comprises an acrylate based system that contains at least one monomer of acrylic acid or methacrylic acid, at least one ester of an acrylate, and a polyurethane.

3. The aerosol hairspray product of claim 1, wherein the ratio of the vapor tap area to the dip tube orifice area is from about 0.063 to about 0.09.

4. The aerosol hairspray product of claim 1, wherein the ratio of the vapor tap area to the dip tube orifice area is from about 0.063 to about 0.08.

5. The aerosol hairspray product of claim 1, wherein the ratio of the vapor tap area to the dip tube orifice area is about 0.063.

6. The aerosol hairspray product of claim 1, wherein the hairstyling formulation comprises from about 40% to about 50% of the dimethyl ether propellant, by total weight of the hairstyling formulation and the dimethyl ether propellant.

7. The aerosol hairspray product of claim 1, wherein the hairstyling formulation comprises from about 35% to about 60% of the water, by total weight of the hairstyling formulation and the dimethyl ether propellant.

8. The aerosol hairspray product of claim 1, wherein the hairstyling formulation comprises from about 39% to about 54% of the water, by total weight of the hairstyling formulation and the dimethyl ether propellant.

9. The aerosol hairspray product of claim 1, wherein the hairstyling formulation comprises from about 5% to about 8% of the one or more hairstyling polymers, by total weight of the hairstyling formulation and the dimethyl ether propellant.

10. The aerosol hairspray product of claim 1, wherein the hairstyling formulation comprises 0% of the ethanol.

11. The aerosol hairspray product of claim 1, wherein the valve housing does not comprise two or more vapor taps.

12. The aerosol hairspray product of claim 1 wherein the hairstyling formulation further comprises benzyl alcohol and wherein the hairstyling formulation comprises less than 1.5% benzyl alcohol, by total weight of the hairstyling formulation and the dimethyl ether propellant.

13. An aerosol hairspray product comprising:
1) a container (100) comprising a container wall (110) which encloses a reservoir (120), wherein the reservoir (120) comprises from about 40% to about 70% of a hairstyling formulation and from about 30% to about 60% of a dimethyl ether propellant, by total weight of the hairstyling formulation and the dimethyl ether propellant;
2) wherein the hairstyling formulation comprises:
    i. from about 30% to about 60% water, by total weight of the hairstyling formulation and the dimethyl ether propellant;
    ii. from about 5% to about 15% hairstyling polymer by total weight of the hairstyling formulation and the dimethyl ether propellant, wherein the hairstyling polymer is water-soluble and has a molecular weight of less than 200,000 g/mol;
    iii. is substantially free of ethanol;
wherein the hairstyling formulation has a viscosity of from about 2.5 cSt to about 5.5 cSt;
3) a spraying device (200) attached to the container (100) for dispensing the hairstyling formulation (180) from the reservoir (120) of the container (100);
wherein the spraying device (200) is fluidly connected to the reservoir (120);
wherein the spraying device (200) comprises a spray actuator (150) and a valve (130);
wherein the valve (130) comprises a valve housing (140);
wherein the valve housing (140) comprises a vapor tap (160);
wherein the vapor tap (160) comprises a vapor tap area;
wherein a dip tube (170) is fluidly connected to the valve (130);
wherein the dip tube (170) comprises a dip tube orifice (175);
wherein the dip tube orifice (175) comprises a dip tube orifice area;
wherein the ratio of the vapor tap area to the dip tube orifice area is from about 0.005 to about 0.011;
wherein the vapor tap area to dip tube orifice area ratio results in no clogs according to the Aerosol Spray Clog Measurement Method.

14. The aerosol hairspray product of claim 13 wherein the hair styling formulation comprises:
from about 5% to about 8% of one or more hairstyling polymers by total weight of the hairstyling formulation and the dimethyl ether propellant, wherein the one or more hairstyling polymers is water-soluble and has a molecular weight of less than 200,000 g/mol, wherein the one or more hairstyling polymers comprises an acrylate based system that comprises at least one monomer of acrylic acid or methacrylic acid, at least one ester of an acrylate, and a polyurethane.

15. The aerosol hairspray product of claim 13, wherein the ratio of the vapor tap area to the dip tube orifice area is from about 0.007 to about 0.011.

16. The aerosol hairspray product of claim 13, wherein the ratio of the vapor tap area to the dip tube orifice area is about 0.011.

17. The aerosol hairspray product of claim 16, wherein the hairstyling formulation comprises 0% of the ethanol.

18. The aerosol hairspray product of claim 16, wherein the hairstyling formulation comprises from about 39% to about 54% of the water, by total weight of the hairstyling formulation and the dimethyl ether propellant.

19. The aerosol hairspray product of claim 16 wherein an ejected composition is sprayed at a delivery rate of from about 0.30 g/sec to about 0.50 g/sec.

20. The aerosol hairspray product of claim 19 wherein the ejected composition comprises particles having a Dv50 droplet size of from about 40 micron to about 100 micron and a Dv90 droplet size of from about 160 micron to about 300 micron.

* * * * *